(12) United States Patent
Gulick

(10) Patent No.: US 12,097,023 B2
(45) Date of Patent: Sep. 24, 2024

(54) DEVICE FOR SENSING DISPLACEMENT DURING A JOINT MOBILIZATION PROCEDURE AND METHOD FOR USING SUCH A DEVICE TO QUANTIFY JOINT MOBILIZATION AND DETECT JOINT LAXITY

(71) Applicant: Therapeutic Articulations, LLC, Spring City, PA (US)

(72) Inventor: Dawn T. Gulick, Spring City, PA (US)

(73) Assignee: THERAPEUTIC ARTICULATIONS, LLC, Spring City, PA (US)

( * ) Notice: Subject to any disclaimer, the term of this patent is extended or adjusted under 35 U.S.C. 154(b) by 951 days.

(21) Appl. No.: 17/124,627

(22) Filed: Dec. 17, 2020

(65) Prior Publication Data

US 2021/0169377 A1 Jun. 10, 2021

Related U.S. Application Data

(63) Continuation-in-part of application No. 15/864,409, filed on Jan. 8, 2018, now Pat. No. 11,123,007.

(60) Provisional application No. 62/443,925, filed on Jan. 9, 2017.

(51) Int. Cl.
*A61B 5/11* (2006.01)
*A61B 5/00* (2006.01)

(52) U.S. Cl.
CPC .......... *A61B 5/1121* (2013.01); *A61B 5/1126* (2013.01); *A61B 5/6806* (2013.01); *A61B 2505/09* (2013.01)

(58) Field of Classification Search
None
See application file for complete search history.

(56) References Cited

U.S. PATENT DOCUMENTS

| | | | | |
|---|---|---|---|---|
| 4,649,934 A * | 3/1987 | Fraser | ............ | A61B 5/103 600/595 |
| 5,156,163 A | 10/1992 | Watkins et al. | | |
| 5,335,674 A * | 8/1994 | Siegler | ............ | A61B 5/103 600/595 |
| 6,890,312 B1 | 5/2005 | Priester et al. | | |
| 8,435,192 B2 * | 5/2013 | Belin | ............ | A61H 1/0237 482/79 |
| 9,289,603 B1 | 3/2016 | Giuffrida et al. | | |
| 11,123,007 B2 | 9/2021 | Gulick | | |
| 2007/0245583 A1 * | 10/2007 | Tindall | ............ | A61B 5/1072 33/511 |
| 2007/0266579 A1 * | 11/2007 | Briscoe | ............ | A61B 5/1071 33/503 |

(Continued)

OTHER PUBLICATIONS

Notice of Allowance issued from the US Patent and Trademark Office in the corresponding U.S. Appl. No. 15/864,409 on Aug. 20, 2021, 9 pages.

(Continued)

*Primary Examiner* — Benjamin S Melhus
(74) *Attorney, Agent, or Firm* — Schott, P.C.

(57) ABSTRACT

A mechanical device is configured to communicate a grade of joint displacement to a clinician during a mobilization procedure on a human or animal joint. The device includes two portions that move relative to one another, when both are engaged to a stable and moveable bone at a joint, and movement of one portion to the other is measured and shown on a display.

20 Claims, 27 Drawing Sheets

(56) References Cited

U.S. PATENT DOCUMENTS

| | | | |
|---|---|---|---|
| 2009/0069733 A1* | 3/2009 | Bonutti | A61H 1/0266 602/21 |
| 2010/0130893 A1 | 5/2010 | Sankai | |
| 2014/0039353 A1 | 2/2014 | Ziegler | |
| 2014/0171834 A1 | 6/2014 | DeGoede et al. | |
| 2014/0260701 A1 | 9/2014 | Imhauser | |
| 2014/0303538 A1 | 10/2014 | Baym et al. | |
| 2015/0022362 A1 | 1/2015 | Lucas | |
| 2015/0342753 A1 | 12/2015 | Donner et al. | |
| 2016/0242646 A1 | 8/2016 | Obma | |
| 2016/0262685 A1 | 9/2016 | Wagner | |
| 2017/0000386 A1 | 1/2017 | Salamatian et al. | |
| 2017/0042465 A1* | 2/2017 | Coelho Do Sameiro Espregueira Mendes | A61B 5/4528 |
| 2017/0086671 A1 | 3/2017 | Sessler | |
| 2017/0265810 A1 | 9/2017 | Van De Vyver | |
| 2017/0340278 A1* | 11/2017 | Imhauser | A61B 5/6835 |
| 2018/0192938 A1 | 7/2018 | Gulick | |
| 2018/0199881 A1 | 7/2018 | Yu et al. | |
| 2023/0181098 A1* | 6/2023 | Imhauser | A61B 5/6835 606/88 |

OTHER PUBLICATIONS

Non Final Office Action issued from the US Patent and Trademark Office in the corresponding U.S. Appl. No. 15/864,409 on May 10, 2021, 12 pages.

Final Office Action Issued from the US Patent and Trademark Office within the U.S. Appl. No. 15/864,409 mailed on Jan. 1, 2021, 18 pages.

Non Final Office Action Issued from the US Patent and Trademark Office within the U.S. Appl. No. 15/864,409 mailed on Aug. 18, 2020, 17 pages.

* cited by examiner

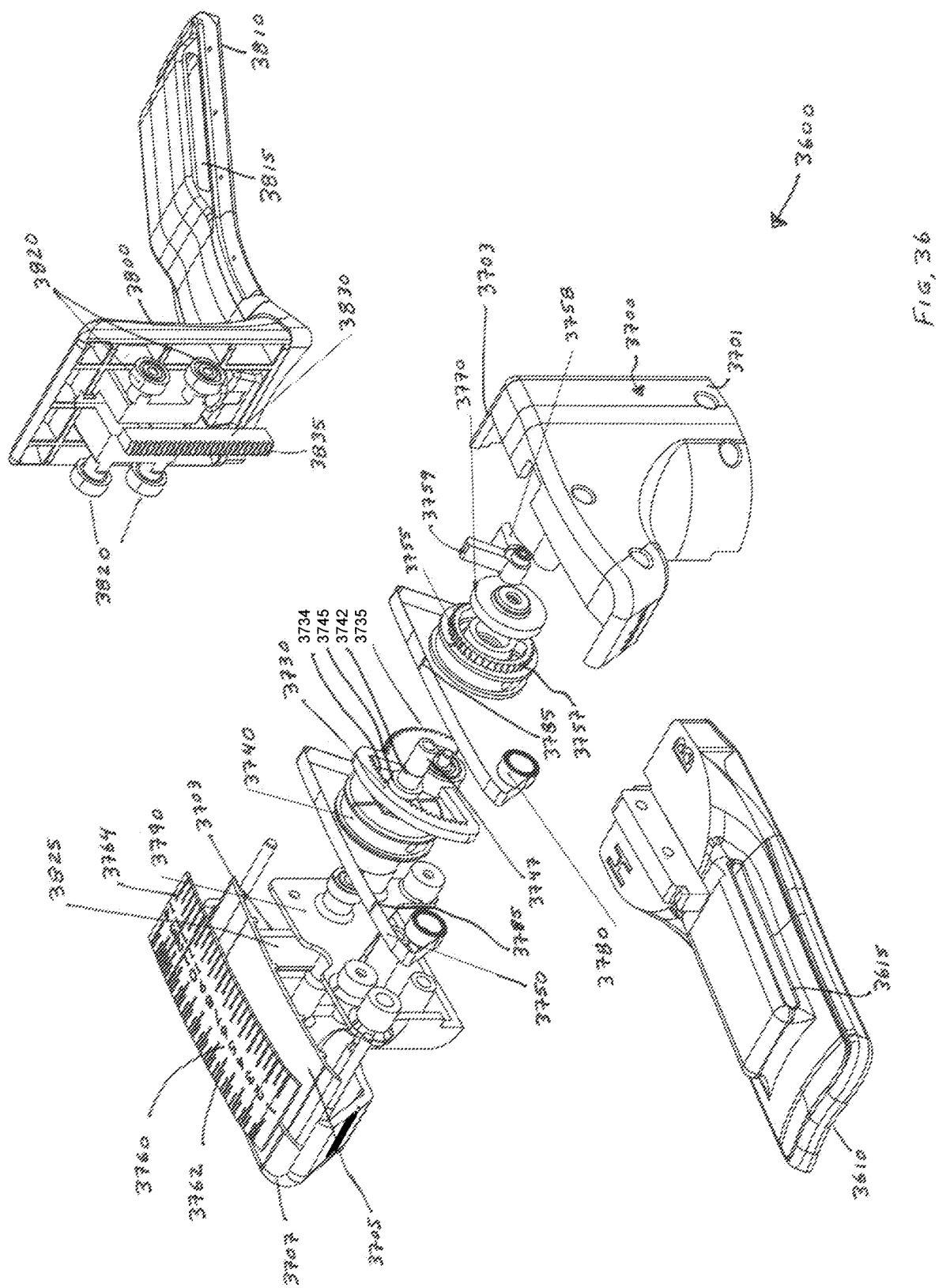

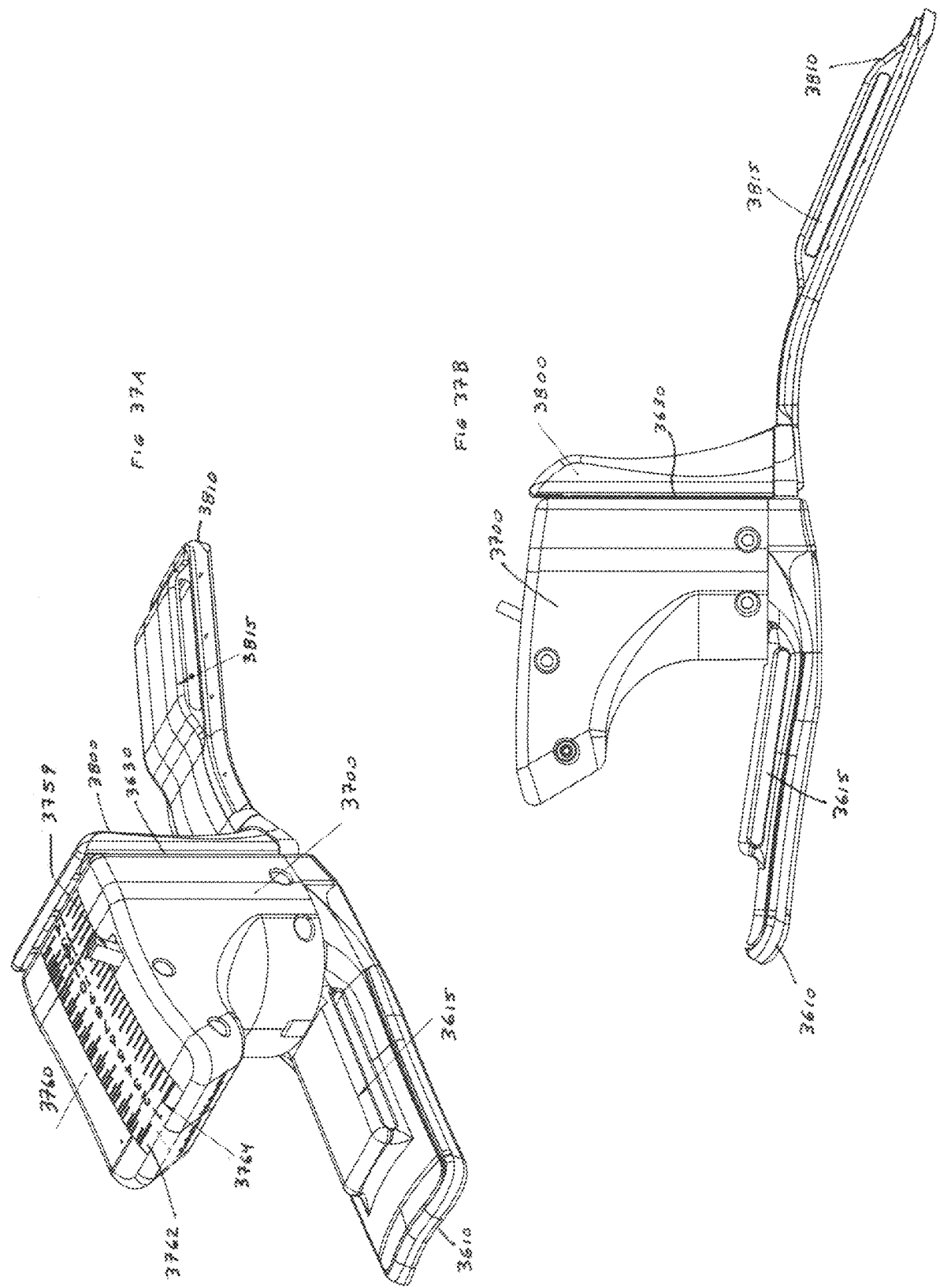

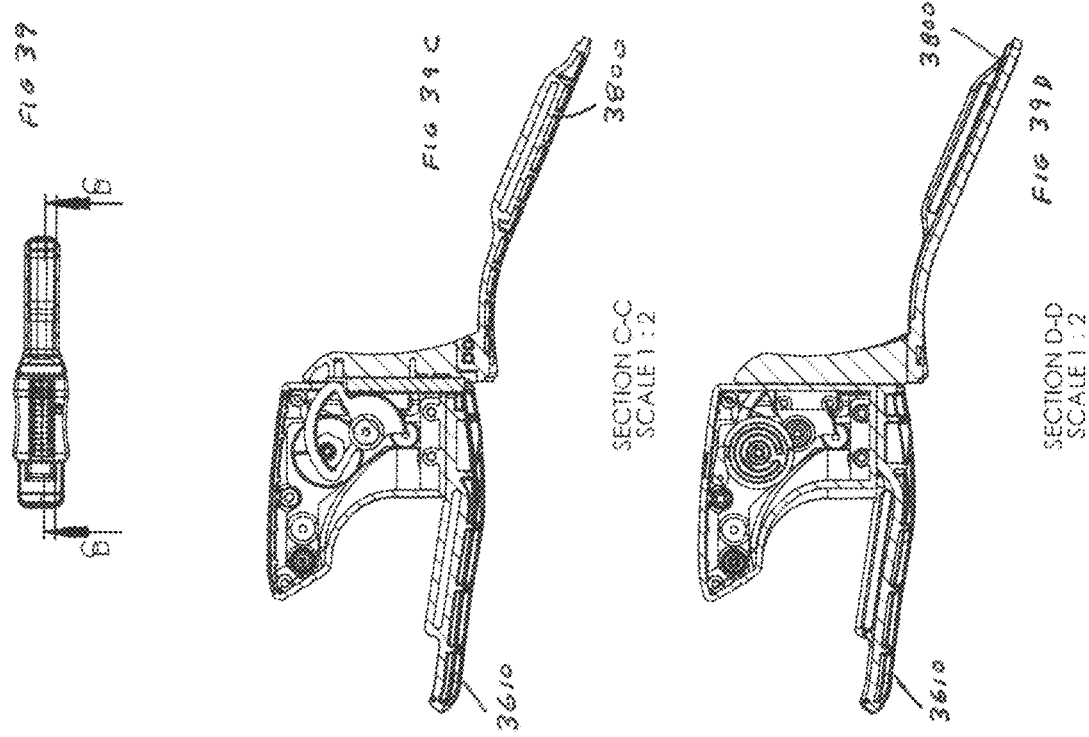
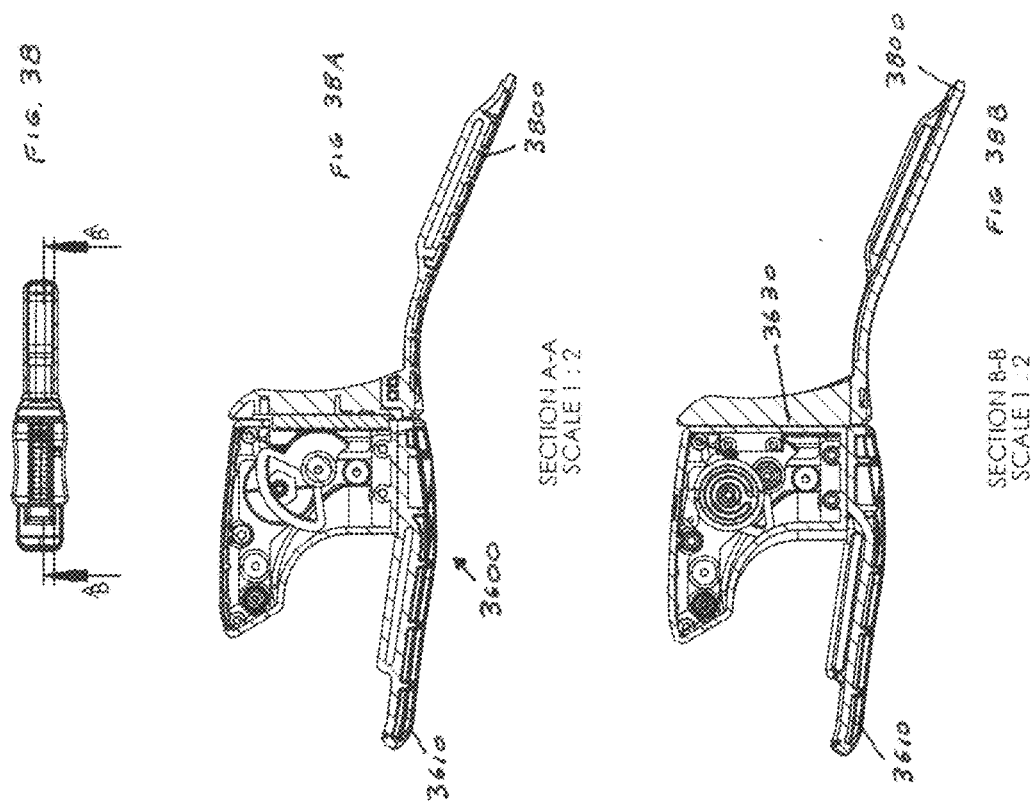

DEVICE FOR SENSING DISPLACEMENT DURING A JOINT MOBILIZATION PROCEDURE AND METHOD FOR USING SUCH A DEVICE TO QUANTIFY JOINT MOBILIZATION AND DETECT JOINT LAXITY

BACKGROUND

The application relates generally to a device used to quantify grades of joint mobilization and detect joint laxity. More specifically, the application relates to a device used by a clinician that provides feedback indicative of the quantity or grade of joint displacement during joint mobilization and testing.

Joint mobilization is a technique routinely used by clinicians, such as physical therapists, to address pain and mobility limitations related to musculoskeletal injury. During joint mobilization, a joint of an injured area of the body is manually moved by the clinician. An exemplary joint mobilization technique involves the linear translation of one joint surface on another, as shown in FIGS. 1A and B. Joint mobilization is typically classified into one of four (4) grades of mobilization. Criteria for each four (4) grades of joint mobilization (I-IV) are clearly defined FIG. 2. As shown, the grades in this example are defined by the degree of applied force and displacement, as a percentage of total range of motion. In practice, the grades of joint mobilization can be challenging to identify accurately, and as a result, the clinical application of these techniques has been reported to be quite variable. This lack of consistency can have a significant effect on patient outcomes. Furthermore, previous methods of measuring joint mobility were expensive, with large equipment that was not easily portable, adaptable to different sized patients or joints, and/or required the clinician to lose visual or touch contact with the patient during use.

A need therefore exists, to accurately identify the grade of joint mobilization undergone during treatment.

SUMMARY OF THE EMBODIMENTS

A medical device to communicate a grade of joint mobilization during a mobilization procedure on a joint, includes a main base body portion; a proximal body portion engaged to the main base body portion through rollers and slots such that the main base body portion and proximal body portion move relative to one another; a mechanical measurement gearing that moves a measurement spool when the base body portion and proximal body portion move with respect to one another; and a measurement tape that moves when the mechanical measurement gearing moves and indicates a measure of movement of the main base body portion and proximal body portion to one another.

BRIEF DESCRIPTION OF THE DRAWINGS

FIGS. 36, 37A, and 37B show exploded and assembled views of the mechanical device.

FIGS. 38, 38A, and 38B show the mechanical device with cross sections in the up/zero measurement position.

FIGS. 39, 39C, and 39D show the mechanical device with cross sections in the down/14 mm measurement position.

DETAILED DESCRIPTION OF THE EMBODIMENTS

Figure 1A:
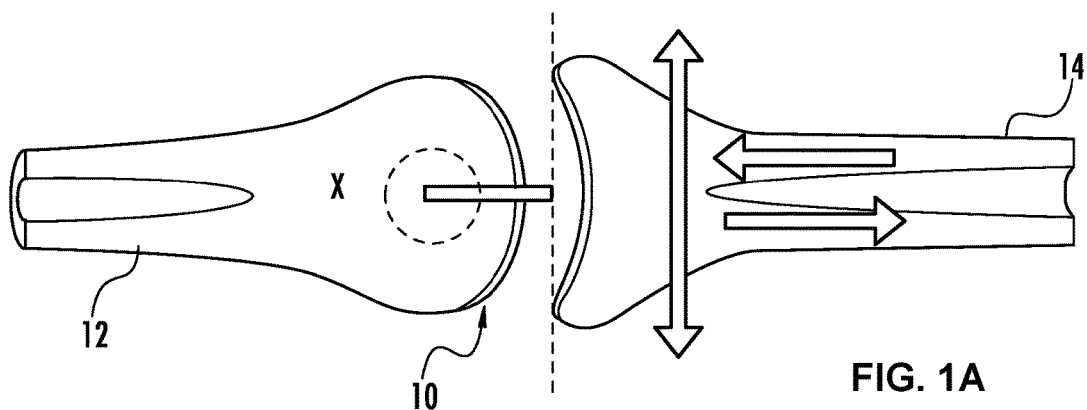
FIGS. 1A-B are cross sectional views showing a joint in two positions during a joint mobilization procedure.

Certain terminology is used in the foregoing description for convenience and is not intended to be limiting. Words such as "front," "back," "top," and "bottom" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 1B:
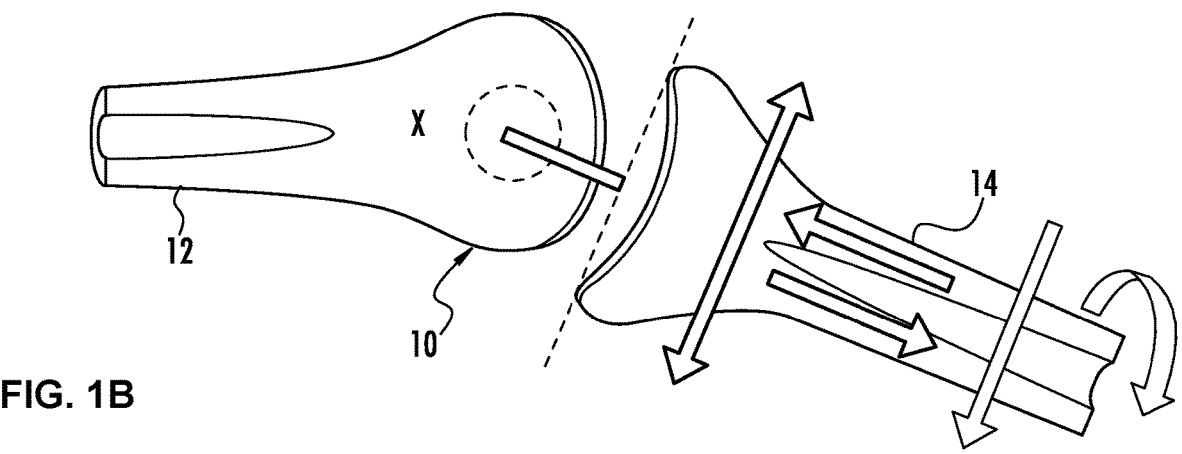

FIGS. 1A and 1B show a joint 10 connecting two bones 12, 14 of a human body during a joint mobilization procedure. The joint 10 illustrated is intended to be exemplary and could be any joint that connects two bones, such as an elbow, knee, hip, shoulder, etc. Furthermore, the joint need not be in a human, but could be in an animal. As shown, the joint 10 comprises a stabilized bone 12 and a mobile bone 14. During a joint mobilization procedure, the stabilized bone 12 is retained in a fixed position by a clinician performing the procedure, while the mobile bone 14 is displaced with respect to the stabilized bone 12, by translating in the illustrated embodiment. FIG. 1A shows the joint 10 in a first stage of such a joint mobilization procedure, in which the stabilized bone 12 and the mobile bone 14 are in linear alignment. FIG. 1B shows the joint in a second stage of the joint mobilization procedure, in which the mobile bone 14 has been translated with respect to the stabilized bone 12. As shown in the figures, the direction of mobilizing forces changes when the joint is moved out of neutral position. The dotted line in figures represents the treatment plane.

Figure 2:
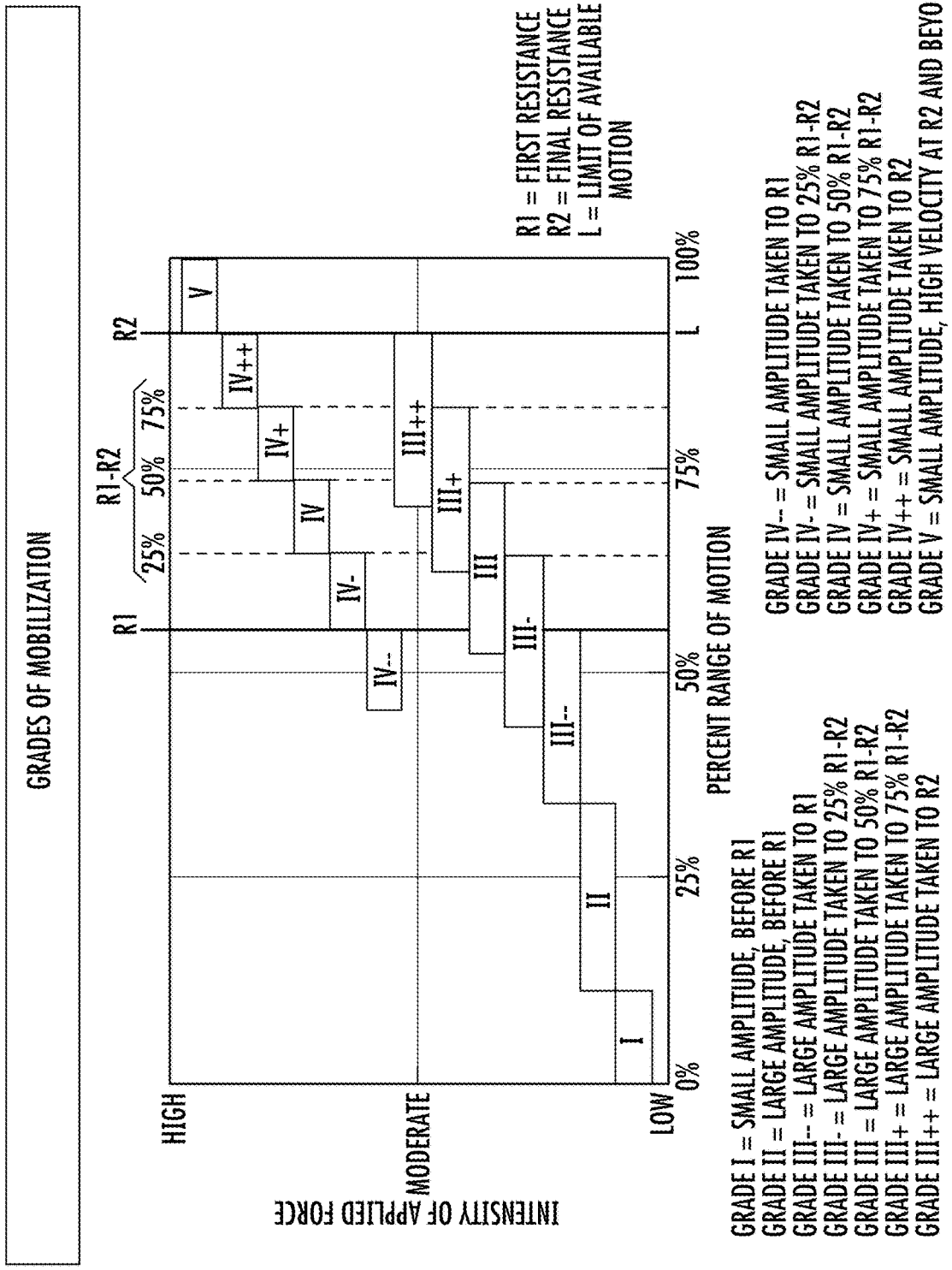
FIG. 2 is a graph of force/linear displacement applied to a joint against percentage of full range of motion, during each of four grades of joint mobilization.

FIG. 2 is a graph showing four exemplary grades of mobilization which may be used as a reference during joint mobilization. As shown, a patient's full range of motion of a mobile bone 14 with respect to a stabilized bone 12 is taken into consideration in determining the four grades of mobilization specific to that patient. Each of the grades, I-IV are determined as a function of position, taken with respect to the patient's full range of motion, versus intensity of the force applied to place the mobile bone in such a position. Different grades of joint mobilization may be applied during treatment based on the desired outcome and stage of treatment. In another embodiment, the grades of mobilization are simply determined by dividing the full range of motion of the mobile bone 14 with respect to the stabilized bone 12 by four. In addition, the grades of mobilization reflect the magnitude of the oscillations within the defined quartile of available motion, i.e. Grade I is in the first quartile of motion and are small oscillations of movement, Grade II is into the second quartile and utilizes larger amplitudes of oscillations, Grade III is in the third quartile with similar amplitudes as Grade II, and finally Grade IV is at the end of the available range/fourth quartile with small amplitude oscillations (similar to Grade I).

Figure 3:
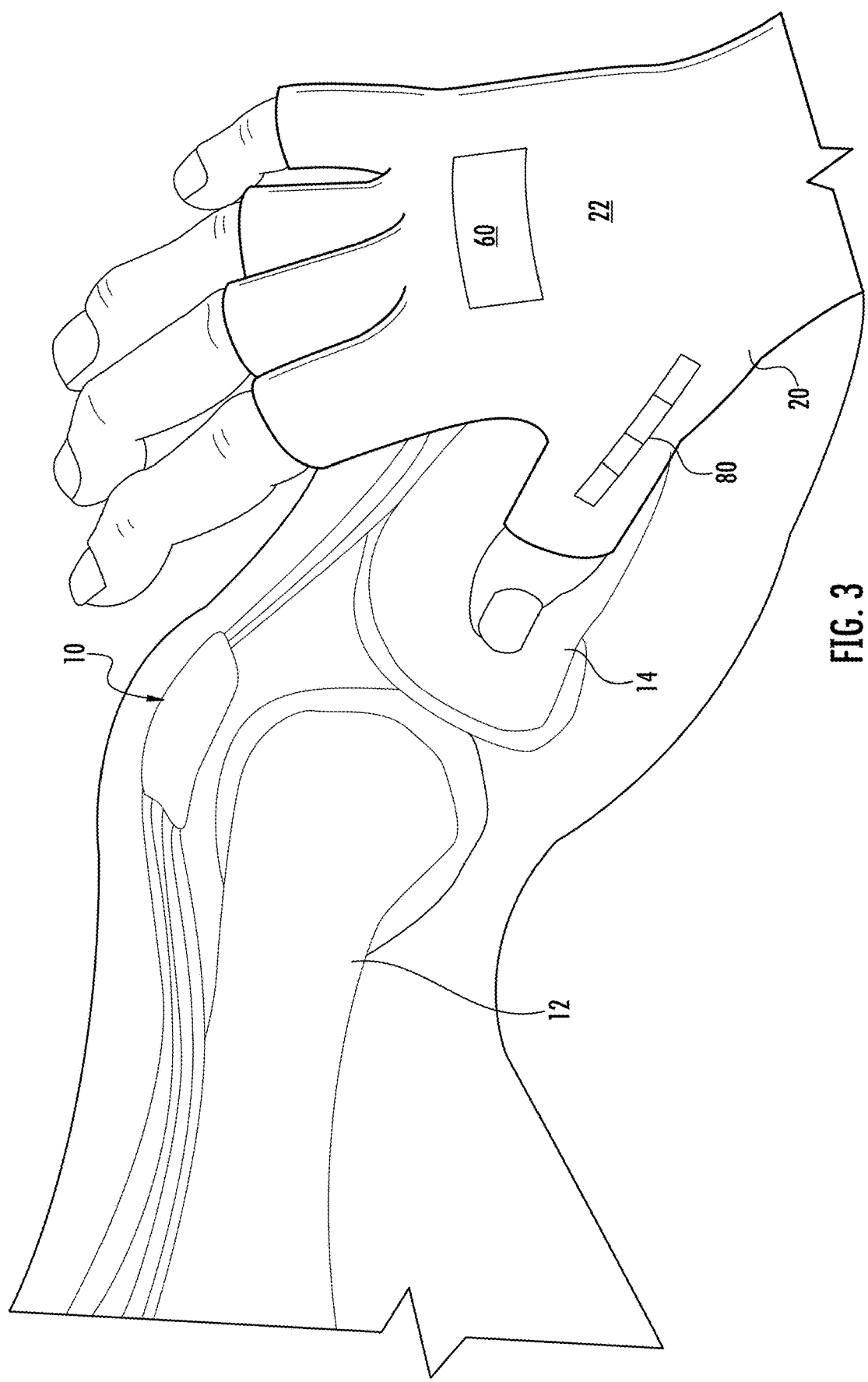
FIG. 3 is a perspective view of a glove according to the invention, as worn on a clinician's hand during a joint mobilization procedure.
Figure 4:
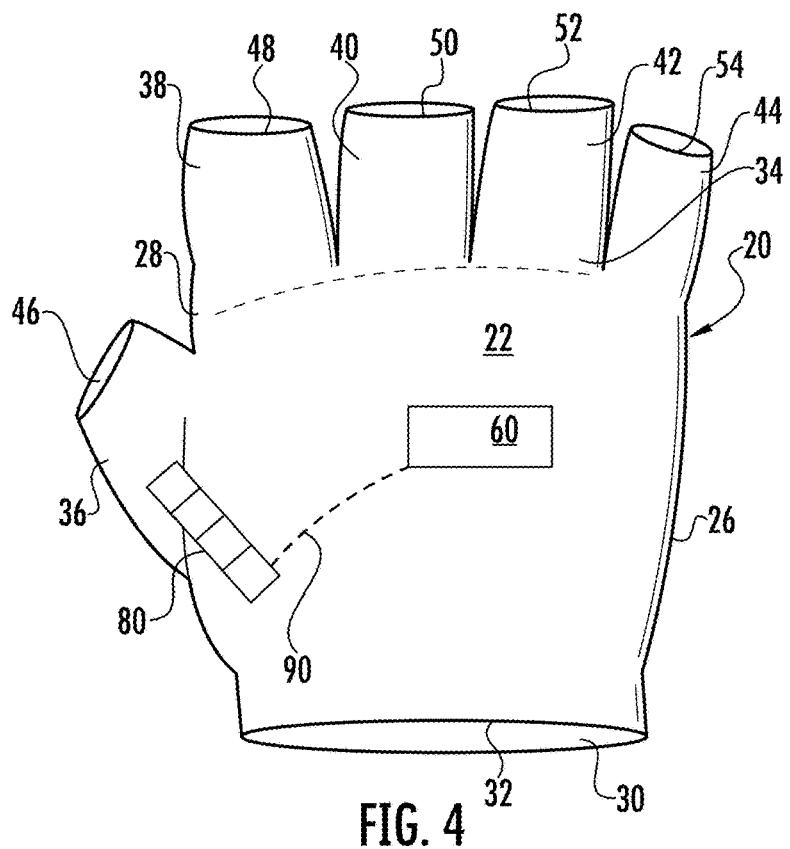
FIG. 4 is a top plan view of the glove of FIG. 3.
Figure 5:
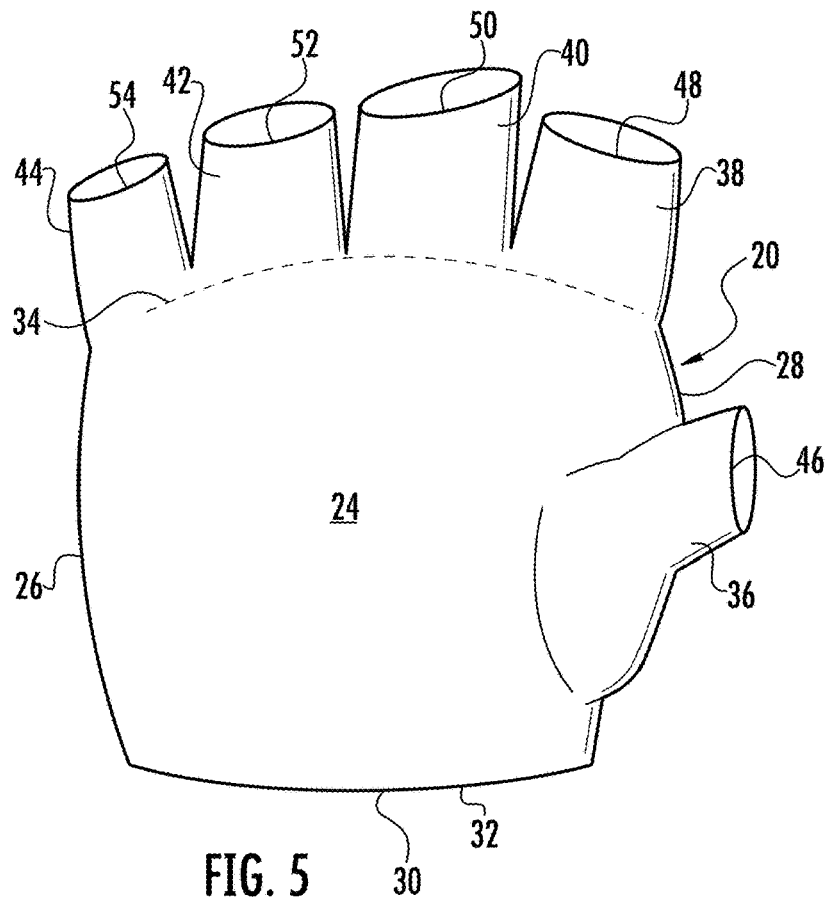
FIG. 5 is a bottom plan view of the glove of FIG. 3.

FIGS. 3-5 show an exemplary embodiment of a glove 20 according to the invention. As shown, the glove 20 comprises a dorsal side 22 that comes in contact with the outer, or dorsal side of a wearer's hand, and a palm side 24 that comes in contact with the palm of a user's hand. The dorsal side 22 and the palm side 24 are joined at opposite edges 26, 28, to form a glove body, which is configured as a closed loop of fabric that surrounds the clinician's hand during wear. A first edge 26 joins the dorsal side 22 and the palm side 24 and is oriented on the outer edge, or pinky side edge, of a wearer's hand, while a second edge 28 joins the dorsal side 22 and the palm side and is oriented on the inner edge, or thumb side edge, of a wearer's hand.

The glove 20 further comprises a lower edge 30 defining a wrist opening 32 through which a wearer's wrist passes during wear. An upper edge 34 is located opposite the lower edge 30. Five finger portions 36, 38, 40, 42, 44 extend outward from the upper edge 34 and are configured for receiving a wearer's fingers during wear, a first finger portion 36 being configured to receive the wearer's thumb, a second finger 38 portion being configured to receive the wearer's index finger, a third finger portion 40 being configured to receive the wearer's middle finger, a fourth finger portion 42 being configured to receive the wearer's ring finger, and a fifth finger portion 44 being configured to receive the wearer's pinky finger. As shown, each finger portion is formed as a tube configured to receive the associated finger. Preferably, as shown in FIGS. 3-5, the finger portions are truncated, such that each comprises an opening 46, 48, 50, 52, 54 that allows the outer portion of the associated finger to pass therethrough, exposing the outer portions and tips of the wearer's fingers. Such a configuration allows the outer portions of the clinician's fingers, including fingertips, to come in contact with a joint undergoing mobilization, as described in detail below.

As shown in FIGS. 3 and 4, the glove 20 further comprises a sensor 60. The sensor 60 detects position and motion of the glove 20, and in use during a joint mobilization procedure, position and motion of the mobile bone 14, as described in detail below. As shown, the sensor 60 is positioned on the dorsal 22 side of the glove body. In use, the palm side 24 of the glove body will likely come into contact with the patient. Placement of the sensor 60 on the dorsal side of the glove body avoids the sensor 60 coming into contact with the patient's body, which could result in discomfort to the patient, interference with the joint mobilization procedure and/or damage to the sensor 60.

Figure 6:
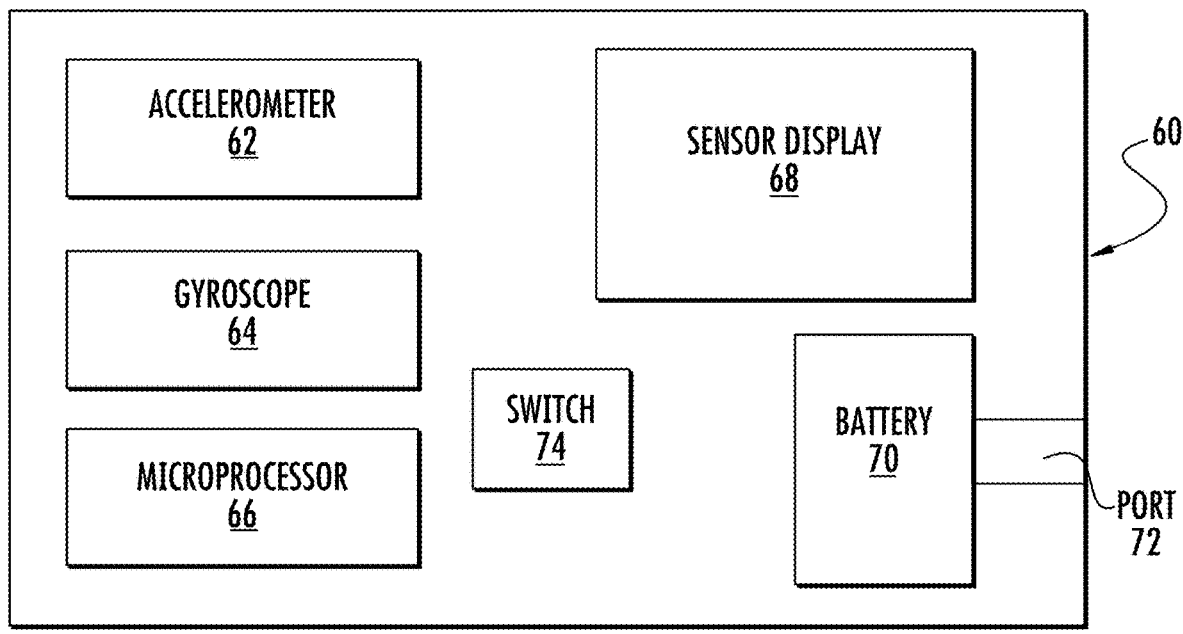
FIG. 6 is a schematic illustration of a sensor according to an embodiment of the invention.

FIG. 6 shows an embodiment of the sensor 60 in detail. As shown, the sensor 60 may comprise an accelerometer 62, gyroscope 64, a microprocessor 66, a sensor display 68, and a battery 70. The sensor 60 is powered by the battery 70, which may be a rechargeable battery. In some embodiments, the sensor 60 may comprise a port 72 that connects the display to an electrical power source for recharging the battery 70, and optionally, as an alternate power source. The accelerometer 62 measures a rate of acceleration of the glove 20. The accelerometer 62 is preferably, multi-axis accelerometer, which may be, for example a three-axis accelerometer that measures the rate of acceleration of the glove 20 in three dimensions. The gyroscope 64 measures an angular orientation of the glove 20. The gyroscope 64 is preferably a three-axis gyroscope that measures angular orientation of the glove 20 in three dimensions. In some embodiments, an accelerometer 62 may be provided without a gyroscope 64. In other embodiments, a gyroscope 64 may be provided without an accelerometer 62. In other embodiments, other types of motion sensors known in the art could be employed in addition to or as an alternative to an accelerometer 62 or gyroscope 64.

Figure 8:
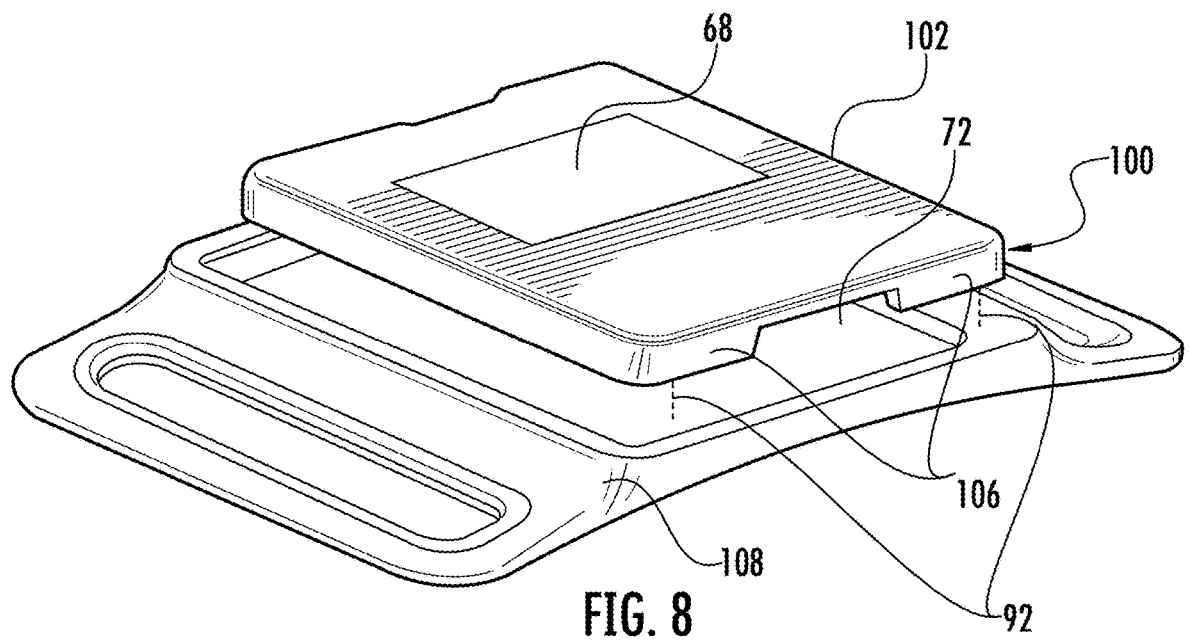
FIG. 8 is an exploded perspective view of a sensor enclosed in a sensor housing according to an embodiment of the invention.
Figure 9:
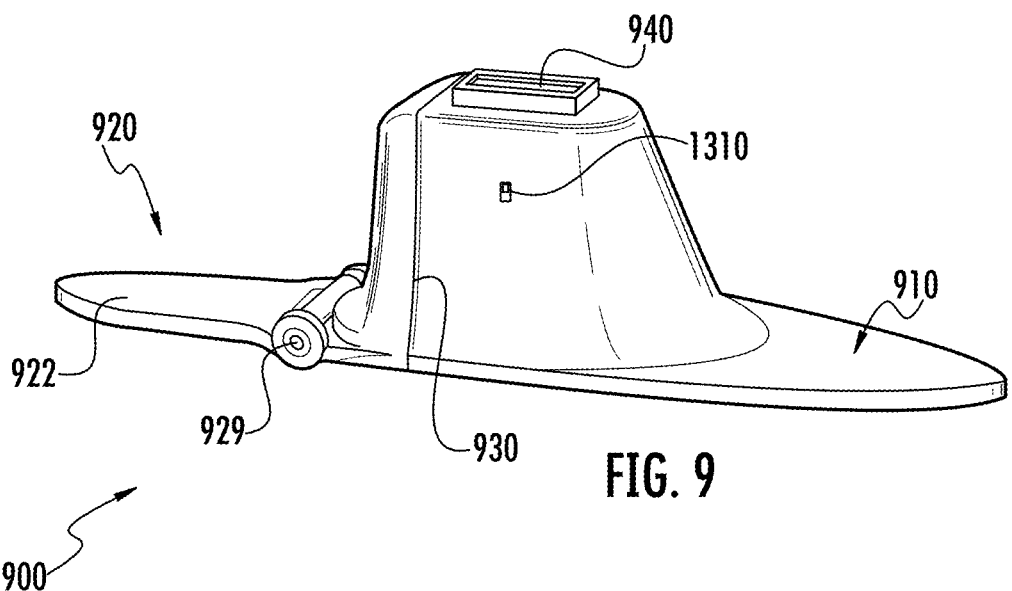
FIGS. 9 and 10 show isometric views of a device for measuring joint displacement.
Figure 10:
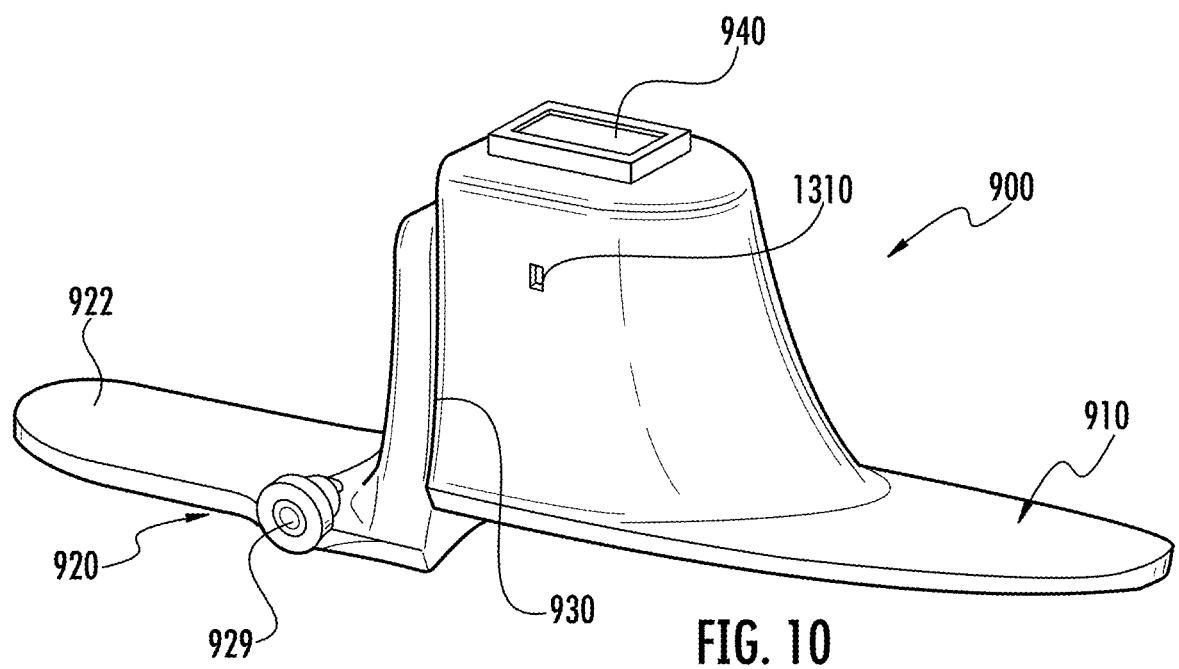
Figure 11A:
FIGS. 11A-D show an alternate embodiment of a distal portion of the device.
Figure 11B:
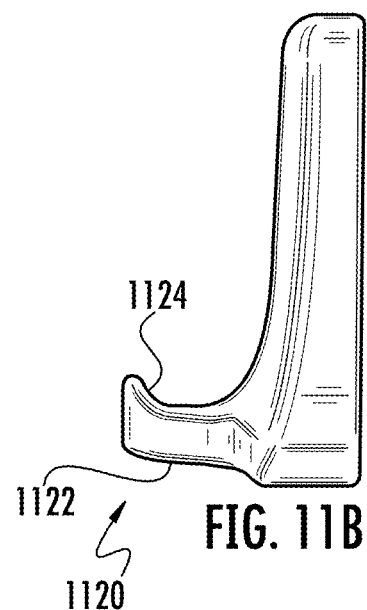
Figure 11C:
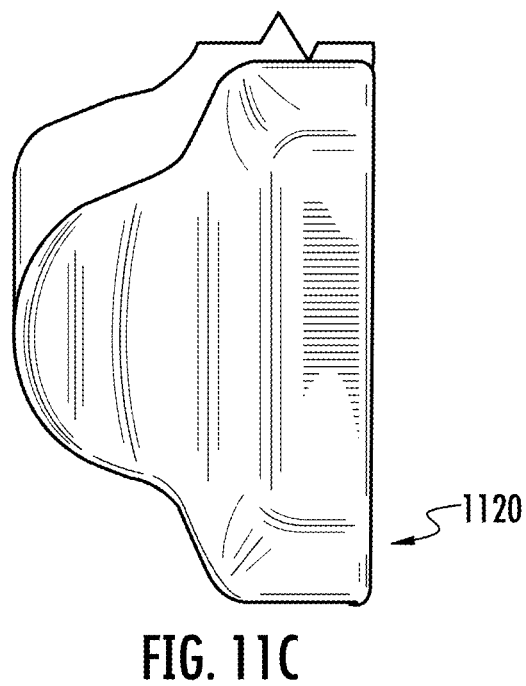
Figure 11D:
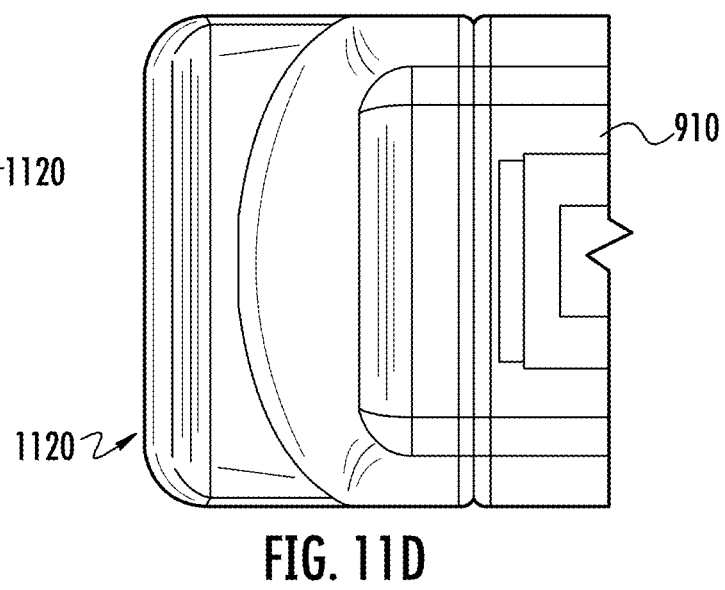

The sensor 60 may be enclosed in a sensor housing 100, such as that illustrated in FIG. 8. As shown, the housing 100 includes an enclosure 102 that fully or partially encloses the sensor 60. The enclosure may be formed of any suitable material, such as a polymeric material. In one embodiment, the enclosure 102 is formed of Acrylonitrile Butadiene Styrene (ABS). As shown, the sensor display 68 is viewable through the enclosure 102. As shown, the port 72 is formed in the sensor housing to facilitate recharging of the battery 70. In one embodiment, the port 72 is a USB port. The enclosure 102 is configured to detachably affix to a receptacle 108. In an embodiment, the enclosure 102 affixes to the receptacle in a snapping engagement, though other means of detachably affixing the enclosure 102 to the receptacle 108 could be employed as well. The receptacle 108 affixes to the glove body. The enclosure 102 may further include terminals 106 and the receptacle 108 may include corresponding contact pads. When the enclosure 102 is affixed to the receptacle 108, the terminals 106 come into contact with the contact pads 106, forming a first end 92 of the connection 90 between the sensor 60 and display 80, as described below.

In use, the accelerometer 62 communicates the acceleration to the microprocessor 66 and the gyroscope 64 communicates the angular position to the microprocessor 66. The microprocessor 66 processes the acceleration and the angular position to determine the position of the glove and optionally the force applied to the mobile bone 14. The microprocessor 66 may optionally also process the angular position to determine an orientation of the glove 20. In some embodiments, the sensor 60 may be provided with a sensor display 68 that displays the position of the glove 20, the orientation of the glove 20, the force being applied to the mobile bone 14, or any combination thereof. In some embodiments, the sensor display 68 is a low power LED display, though other types of displays known in the art could be employed as well.

The sensor 60 may be secured to the glove 20 by any means known in the art, such as adhesives, stitched thread, hook and loop fasteners such as those sold under the trade name VELCRO®, buttons, snaps, and other fasteners known in the art. In some embodiments, the sensor 60 is permanently secured to the glove 20, such as by stitched thread or adhesives. In other embodiments, the sensor 60 is detachably secured to the glove 20, such as by buttons, snaps or hook and loop fasteners. In the embodiment shown in FIG. 8, the sensor 60 is enclosed within a housing 100 that detachably engages snappingly with a receptacle 108 affixed to the glove body. Embodiments in which the sensor 60 is detachably secured to the glove 20 have the advantage of allowing the sensor 60 to be removed during maintenance and/or laundering of the glove 20, avoiding potential damage to the sensor 60 during such processes.

The glove 20 further comprises a display 80 which is in communication with the sensor 60. The display 80 is preferably an LED display, but can also be any type of display known in the art which is capable of providing visual feedback regarding the displacement of the glove 20, as described herein.

Figure 7:
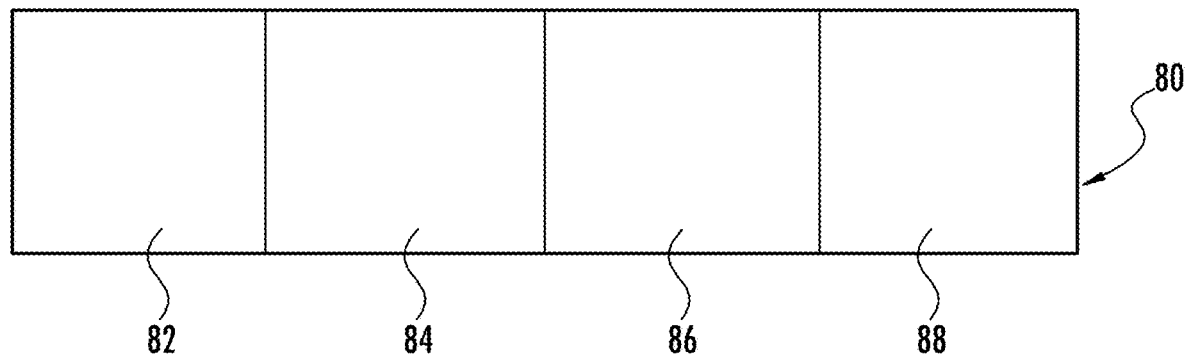
FIG. 7 is a schematic illustration of a display according to an embodiment of the invention.

An embodiment of the display 80 is shown in detail in FIG. 7. The display 80 of the illustrated embodiment comprises four indicators 82, 84, 86, 88, each is which configured to illuminate in a selected color when displacement of the glove 20 is within a selected range. In one embodiment, the display 80 illuminates in each of the four different colors when the displacement of the glove is within an associated one of four different grades of mobilization. For example, the display 80 may include a first indicator 82, which is configured to illuminate in blue when displacement is within a first grade of mobilization, a second indicator 84, which is configured to illuminate in green when the displacement is within a second grade of mobilization, a third indicator 86, which is configured to illuminated in yellow when displacement is within a third grade of mobilization, and a fourth indicator 88, which is configured to illuminate in red when displacement is within fourth grade of mobilization.

In another embodiment, the display could include fewer or more indicators that illuminate in different colors, to indicate when displacement is within fewer or more than four grades of mobilization.

In another embodiment, the display 80 could include a single indicator that is configured to illuminate in multiple colors, each color being associated with a selected grade of mobilization as described above.

As shown, the display 80 is positioned on the dorsal side 22 of the glove body. In use, the palm side 24 of the glove body will likely come into contact with the patient. Placement of the display 80 on the dorsal side of the glove body avoids the display 80 coming into contact with the patient's body, which could result in discomfort to the patient, interference with the joint mobilization procedure and/or damage to the display 80. In the illustrated embodiment, the display 80 is located between the second edge 28 and the sensor 60 on the dorsal side 22 of the glove body. Such placement of the display 80 makes it easily viewable to a clinician during joint mobilization, during which the thumb side of the hand is often located facing the clinician, and therefore most easily viewable. In other embodiments, the display 80 may be located on other areas of the glove body. In other embodiments, the display 80 may be attachable at different areas of the glove body. In yet other embodiments, the display 80 could be detached from the glove body and optionally affixed to a separate structure.

The display 80 may be secured to the glove 20 by any means known in the art, such as adhesives, stitched thread, hook and loop fasteners such as those sold under the trade name VELCRO®, buttons, snaps, and other fasteners known in the art. In some embodiments, the display 80 is permanently secured to the glove 20, such as by stitched thread or adhesives. In other embodiments, the display 80 is detachably secured to the glove 20, such as by buttons, snaps or hook and loop fasteners. Embodiments in which the display 80 is detachably secured to the glove 20 have the advantage of allowing the display to be removed during maintenance and/or laundering of the glove 20, avoiding potential damage to the display 80 during such processes.

The sensor 60 communicates the position of the glove 20 to the display 80 via a connection 90. In the illustrated embodiment, the connection 90 is a wired connection through which the sensor 60 transmits at least one signal indicative of the grade of mobilization. In other embodiments the connection 90 could be a wireless connection.

In some embodiments, the microprocessor 66 generates a position signal, indicative of the position of the glove 20 and transmits the signal to the display 80 via the connection 90. In some embodiments, the display 80 illuminates in a selected color, as described above, indicative of the grade of mobilization, wherein the grade of mobilization is determined according to the position, or degree of displacement of the glove, and in turn the mobile bone 14. The display 80 may then illuminate in blue during Grade I mobilization, in green during Grade II mobilization, in yellow during Grade III mobilization and in red during Grade IV mobilization, wherein Grade I mobilization is a first displacement range, Grade II is a second displacement range greater than the first displacement range, Grade III is a third displacement range greater than the second displacement range, and Grade IV is a fourth displacement range greater than the third displacement range.

The microprocessor 66 may optionally also process the force applied to the mobile bone 14, in order to determine the grade of mobilization in accordance with the chart of FIG. 2. In such embodiments, the microprocessor 66 processes the position of the glove 20 and the force being applied, as described below, to generate a mobilization signal, indicative of the grade of mobilization, as determined according to the chart of FIG. 2, i.e., taking force and displacement into account, and transmits the mobilization signal to the display 80. The display 80 may then illuminate in a selected color, as described above, indicative of the grade of mobilization, i.e., the display 80 illuminates in blue during Grade I mobilization, in green during Grade II mobilization, in yellow during Grade III mobilization and in red during Grade IV mobilization.

In one embodiment, the microprocessor 66 generates an orientation signal, indicative of orientation of the glove 20, and transmits the orientation signal to the display 80 via the connection 90. In such an embodiment, the orientation of the glove 20 could be determined by a gyroscope 64 comprised in the sensor 60, as described above. The display 80 may indicate the orientation of the glove 20 or may provide a user with a visual or other warning when the angular orientation of the glove 20 is outside of a desired range.

A method for using a glove 20 according to the invention is as follows. A user or clinician places the glove 20 on the hand expected to contact a patient's mobile bone 14 during a joint mobilization procedure. The clinician uses the opposite hand to stabilize the adjacent bone, referred to herein as the stabilized bone 12. The clinician then performs a test mobilization to determine the full range of motion of the mobile bone 14 with respect to the stabilized bone 12. In one embodiment, the sensor 60 may be provided with means to communicate with the microprocessor 66 that the mobilization is being performed is a test mobilization, such as a button or switch 74, in which depressing the button or toggling the switch communicates that the mobilization is a test mobilization. The accelerometer 62 senses and communicates to the microprocessor 66 the displacement of the glove 20, and in turn, the mobile bone 14 during the test mobilization. The microprocessor 66 divides the displacement into a selected number of segments, the selected number being four in the exemplary embodiment, though it should be understood that fewer or more segments could be calculated. In one embodiment, each for the segments is equal in length. For example, in such an embodiment, if the full range of motion of the joint is determined to be 10 mm, each segment will extend for 2.5 mm. Each segment will be considered to be an individual grade of mobilization, which may be referred to as Grades I-IV described above.

During subsequent mobilizations executed as a means of treatment ("treatment mobilizations") the clinician will stabilize the adjacent, or stabilized bone 12 using the ungloved hand, and displace the mobile bone 14 using the gloved hand in the manner described above. The microprocessor 66 will transmit a signal indicative of the segment in which the mobile bone 14 is currently located, and the display 80 will display information indicative of the grade of mobilization, for example by illuminating a real-time linear value and/or a selected color to indicate each Grade of mobilization, such as blue for Grade I, green for Grade II, yellow for Grade III, and red for Grade IV.

In embodiments in which the microprocessor processes the force applied in order to determine the grade of mobilization, the display may display information indicative of the grade of mobilization as determined according to the chart of FIG. 2.

In embodiments in which the microprocessor transmits an angular orientation signal to the display, the display may display information indicative of the angular orientation of the glove 20. For example, the display may display a numeric value that quantifies the angular orientation of the glove 20, or may simply communicate a warning when the angular orientation is outside of a predetermined range, which may be an auditory warning, visual warning, tactile warning, or any other type of warning known in the art.

The glove 20 according to the invention may be provided in different sizes and configurations to accommodate different hand sizes. Additionally, the glove could be configured to be worn on the right or left hand. In some embodiments, the sensor 60 and/or display 80 are configured to be attachable to opposite sides of the glove 20 so that it can be worn on either the left or right hand, with the sensor 60 and display 80 being located on the dorsal 22 side thereof. In other embodiments, a pair of gloves 20 according to the invention and configured to accommodate a user's right and left hand could be provided.

FIGS. 9-16 show an alternate embodiment of a mobilization measurement device 900 for measuring joint mobilization and/or linear translation. The mobilization measurement device 900 includes two portions, a stable base component portion 910, and a distal base component portion 920. The distal stable portion 920 moves linearly with respect to the stable distal portion 910 along a joint or seam in the device and measures movement by means of a linear potentiometer, as can be seen comparing the distal portion 920's position between FIGS. 9 and 10.

The distal portion 920 may include an adjustable fin 929 that rotates about an axis 929. The adjustable fin 929 allows the device 900 to be used on different sized and contoured patients and at also different joints. The adjustable fin 929 may be of different sizes and shapes to accommodate different joints and types of patients.

FIGS. 11A-11D show views of another variation of the distal portion. An alternative distal portion 1120 includes a tab 1122 with an upturned flange 1124. In use, this tab 1122 and upturned flange 1124 may help a clinician hold the alternative distal portion 1120 against a patient during translation. Although not shown, this alternative embodiment of an alternative distal portion 1120 may also be rotatable about an axis similar to the axis 929.

Figure 12:
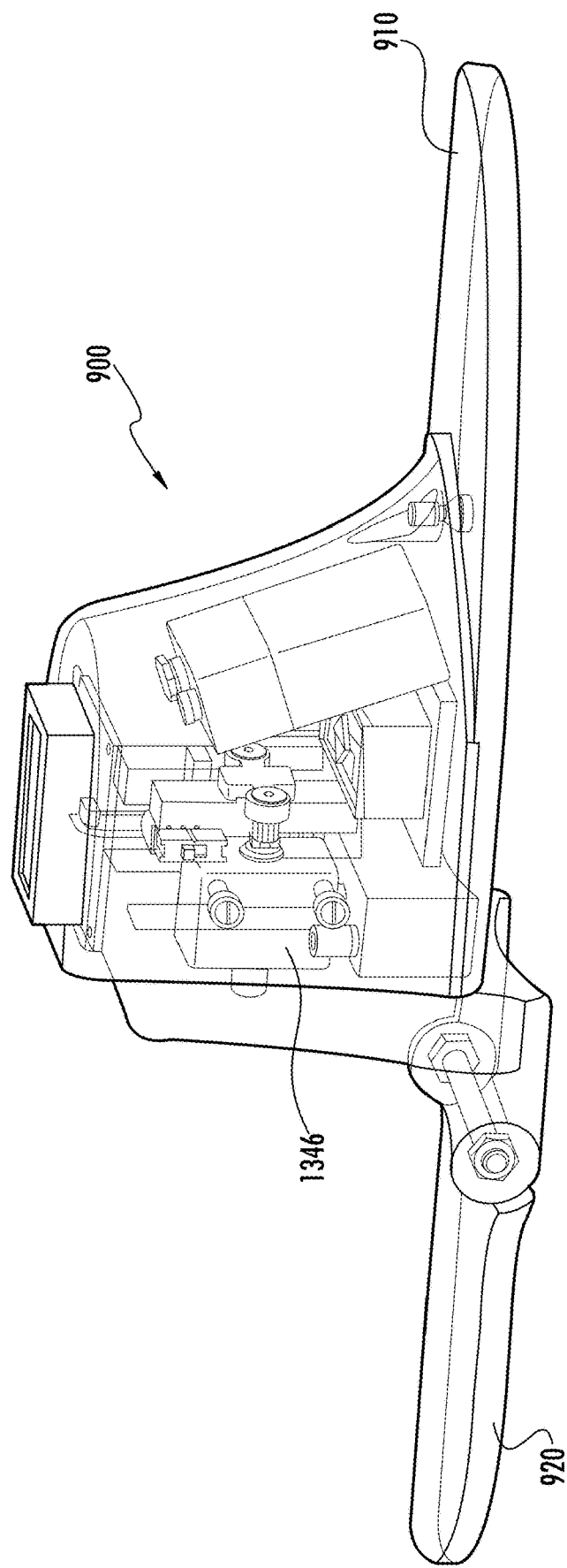
FIGS. 12-16 show exploded interior views within the device.
Figure 13:
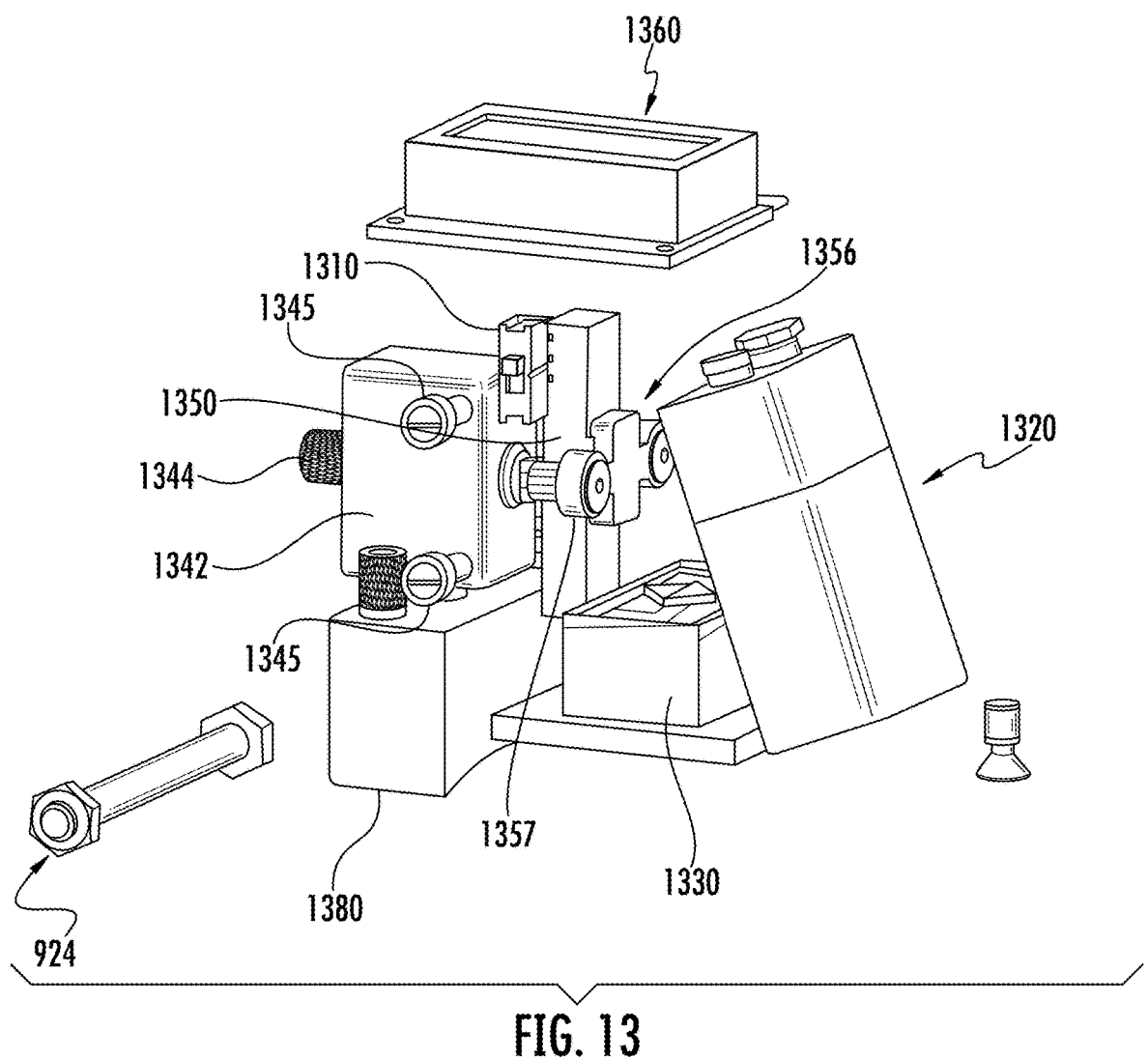
Figure 14:
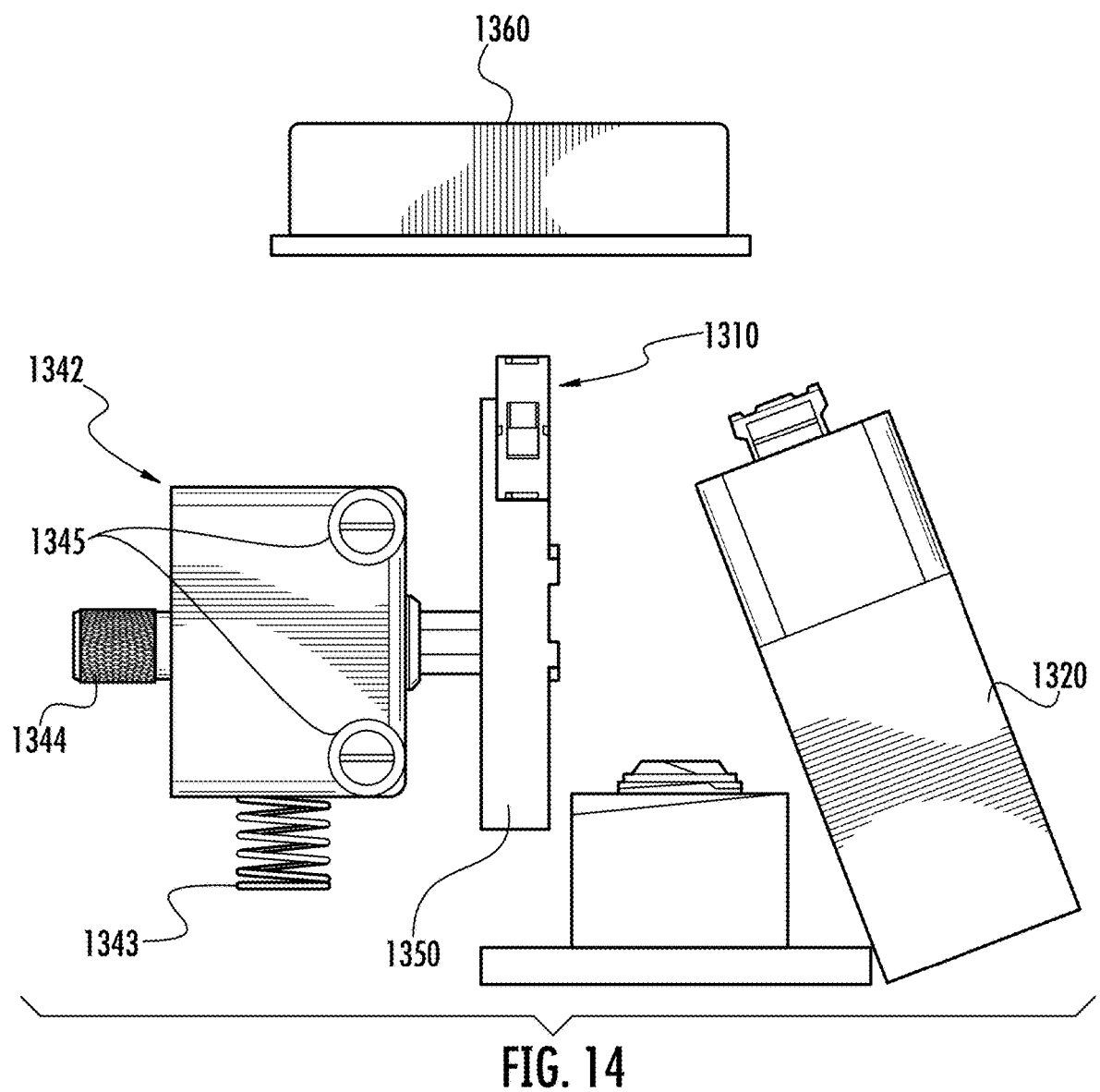
Figure 15:
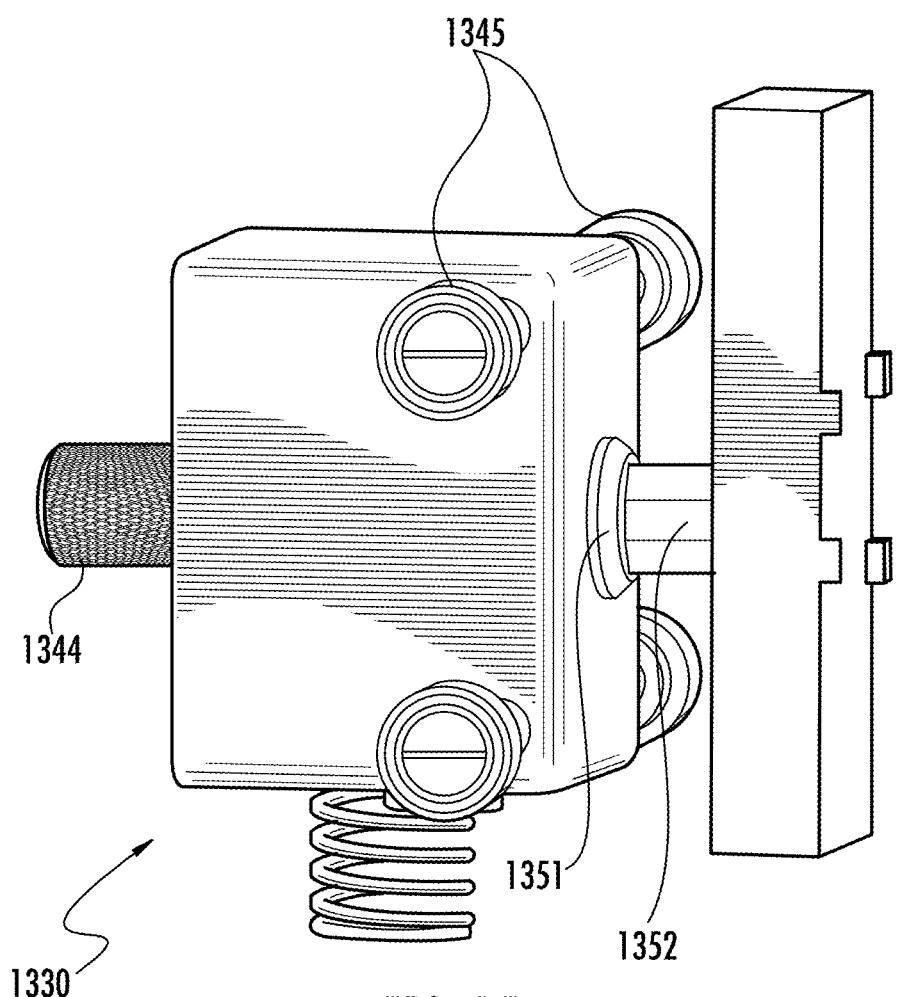
Figure 16:
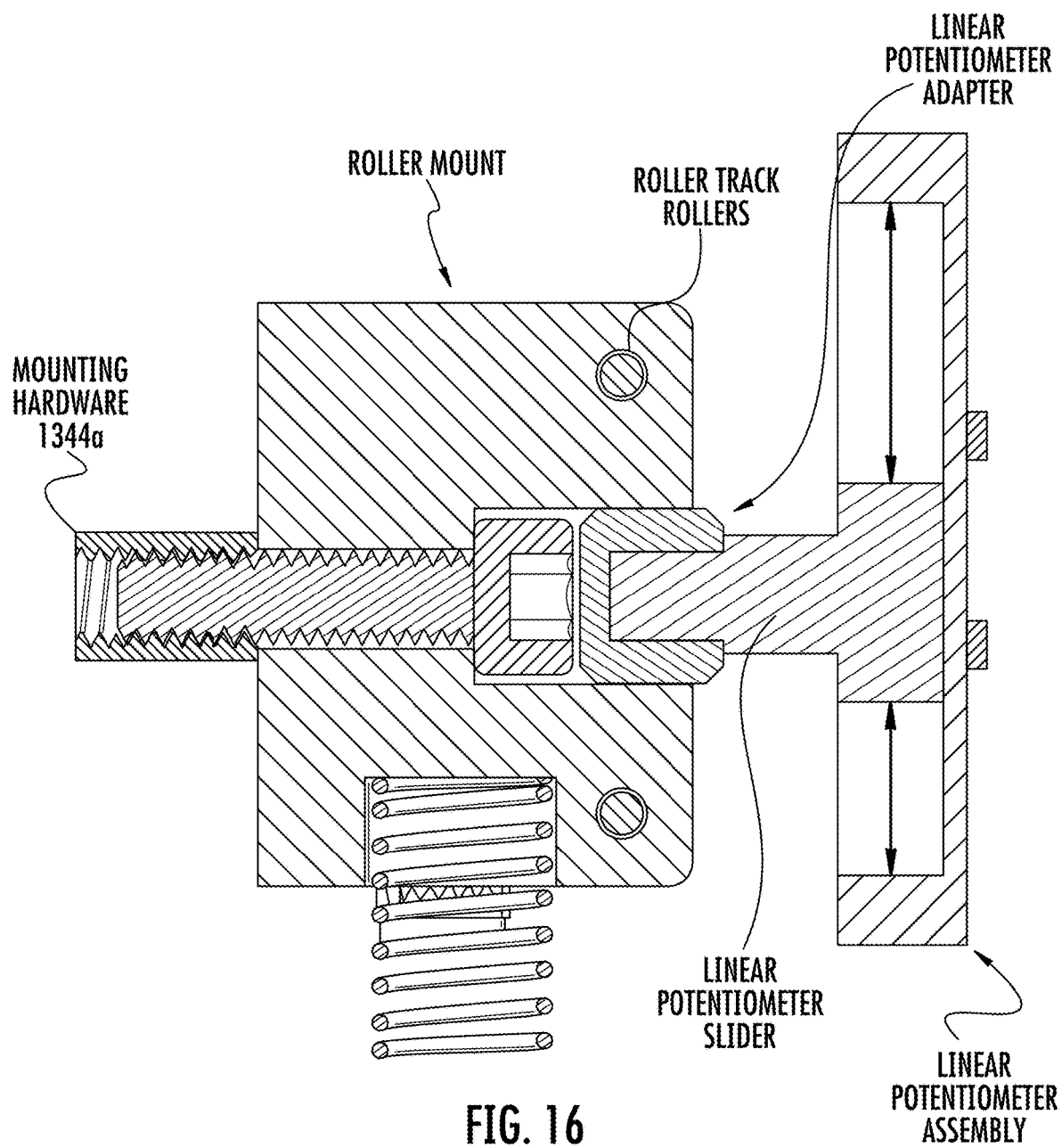

As seen in FIG. 12, in use, a clinician aligns the stable portion 910 with a patient's stabilized bone 12 and the distal portion 920 with the mobile bone 14. The clinician aligns the patent's joint 10 with the device joint or seam 930. The clinician may also align a fin 929 or other specialized attachment to engage the contours of the patient's relevant body part more accurately.

With the device 900 properly aligned on a patient, the clinician ensures that the distal portion 920 engages the patient either through hand pressure or through a strap (perhaps VELCRO™ or other similar fasteners known in the art may be used with both portions on both sides of the joint) or other attachment means and then translates the patient's mobile bone 14 using some form of manual or machine mobilization. Movement of the mobile bone 14 with respect to the stabilized bone 12 results in corresponding movement of the distal portion 920 to the stable portion 910 along the seam 930 of the device 900. The device 900 processes and records the portion 910 and 920s' relative movement to one another and displays a measurement of this movement on the display or screen 940, which may be attached or detached or detachable from the device 900. This measurement may be in units of distance, grades, or other measures as required, but in any event corresponds to the distance that the distal portion 920 moves with respect to the stable portion 910. Measured linear distance could be between 0.0 and 20 millimeters. This measurement may by recorded and saved and then tracked in subsequent mobilizations.

FIGS. 12-16 show interior and exploded views of certain components within the device 900. As best seen in the interior exploded view of FIG. 13, the device 900 includes a power switch 1310 to engage power from a battery 1320 to the power-driven components such as the linear potentiometer assembly 1330 (see FIG. 15), potentiometer 1340, and display 1360.

The potentiometer 1340 includes a roller mount 1342, linear potentiometer 1350 and potentiometer capture 1356. A return spring 1343 extending from the roller mount 1342 engages a housing block 1380 to ensure the distal portion 920 returns to the same level as the stable portion 910 after each translation.

A roller mount bolt 1344 (shown as a knurled mounting hardware 1344a in FIG. 16) extends from the roller mount 1342, which is within the stable portion 910 and engages to the distal portion 920. Because of this engagement, the roller mount 1342 moves through the engagement of the roller mount rollers 1345 to posts (or other means) within the stable portion 910 when the distal portion 920 moves relative to the stable portion 910.

As the roller mount 1342 moves linearly, the linear potentiometer 1350 also moves due to its engagement to the roller mount 1342 through an adaptor 1351 and slider 1352. The linear potentiometer 1350 is engaged to the potentiometer capture 1356 through rollers 1357, and together, motion of one relative to the other is measured within the potentiometer and that measurement or other data is processed and/or transmitted to the screen 1360.

Figure 17:
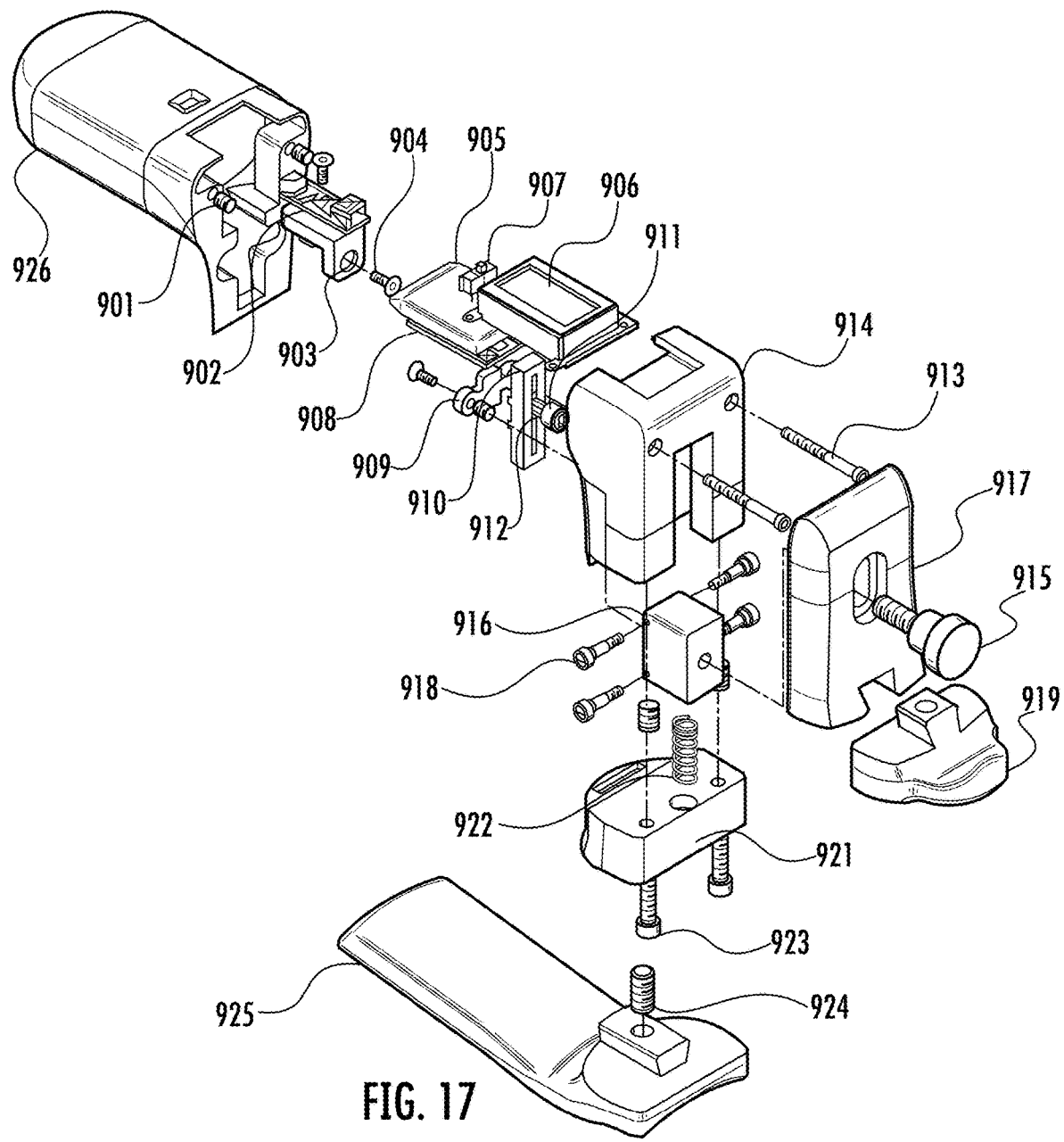
FIG. 17 shows an exploded view of the device.
Figure 18:
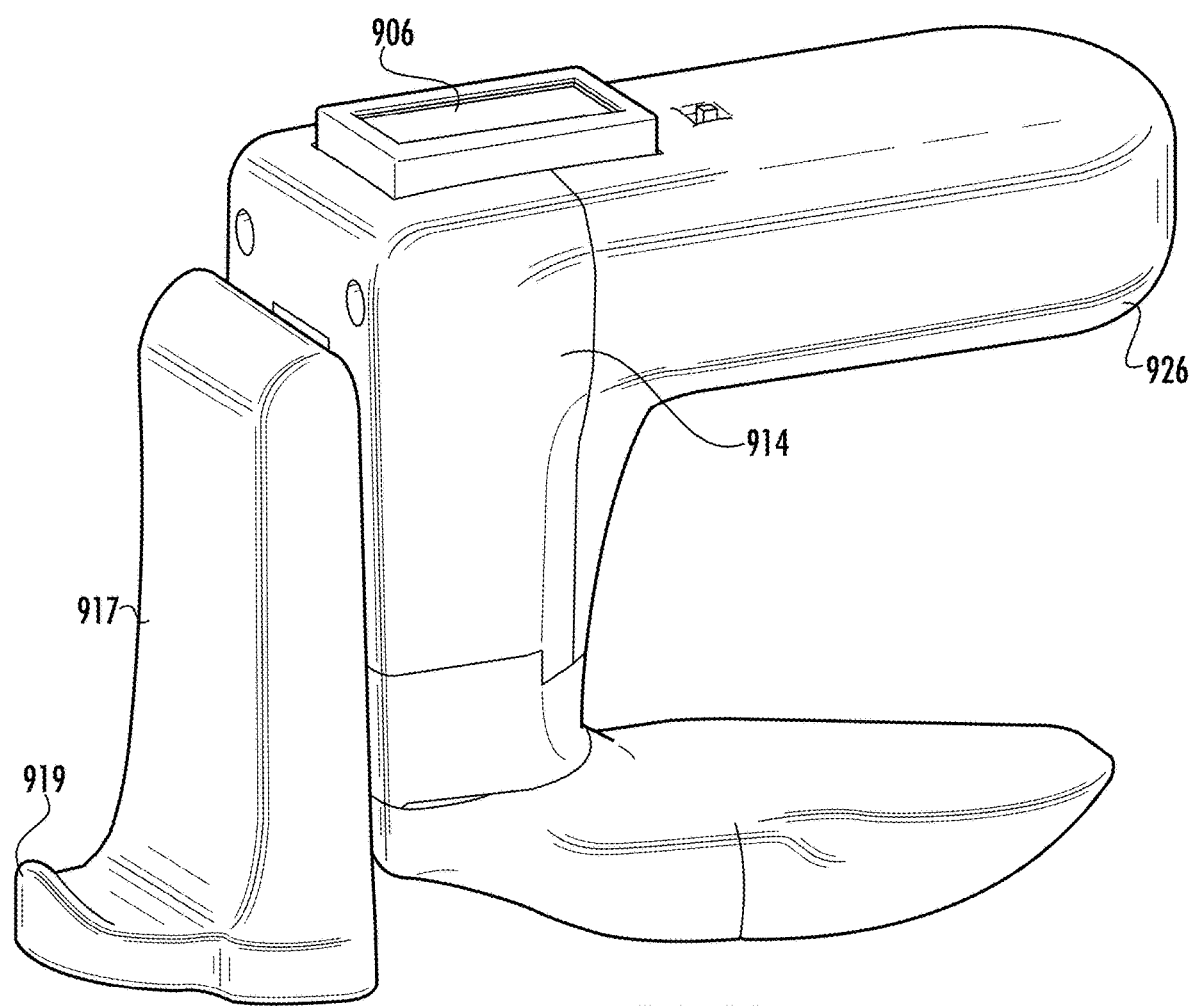
FIG. 18 shows an illustration of one embodiment of the device.

FIGS. 17-18 show alternate embodiments of a mobilization measurement device 900. FIG. 17 is the assembly image of the components of the device in an exploded view, and FIG. 18 is a perspective view of the same. As seen in FIGS. 17-26, the device comprises at least the following: self-clinching nut(s) 901, charger 902, charger adapter block 903, fastener 904, battery 905, LCD display 906, switch lock 907, microprocessor 908, potentiometer hold down 909, linear potentiometer base 910, linear potentiometer arm 911, potentiometer adapter 912, socket head screw(s) 913 and 923, base 914, knob 915, roller mount 916, distal vertical portion 917, track roller 918, distal base optional attachment component 919, track capture 921, compression spring 922, spring plunger 924, attachment for supine knee 925 and base lid 926. The device 900 may be portable, lightweight (weighing under one pound), handheld and adjustable to sit flush against a patient's body regardless of the joint movement being measured. The device 900 allows measurement of linear translation while at the same time keeping physical and visual contact with the soft tissue around the joint, allowing soft tissue feedback.

Figure 19:
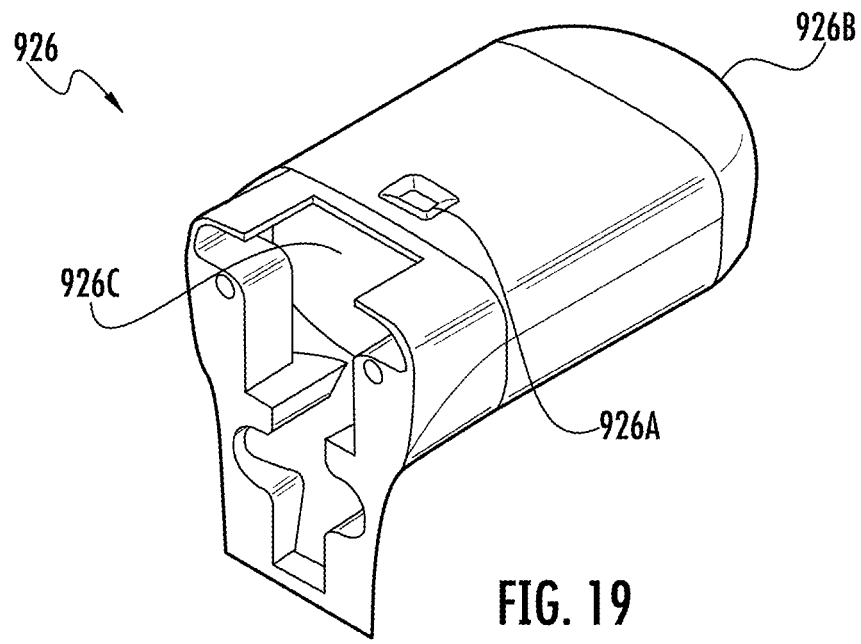
FIG. 19 shows an example of a base lid on the device.

FIG. 19 includes the details of the base lid 926. This custom molded component may comprise an on/off switch for the device 926A, a USB port 926B for the display or LCD, a frame for the display 926C, the adapter block 903, a battery, which may be a lithium battery 905, a microprocessor 908, a linear potentiometer hold down 909, base 910, arm 911, and an adapter 912. In one embodiment, the housing is made of plastic and/or nylon material.

Figure 20:
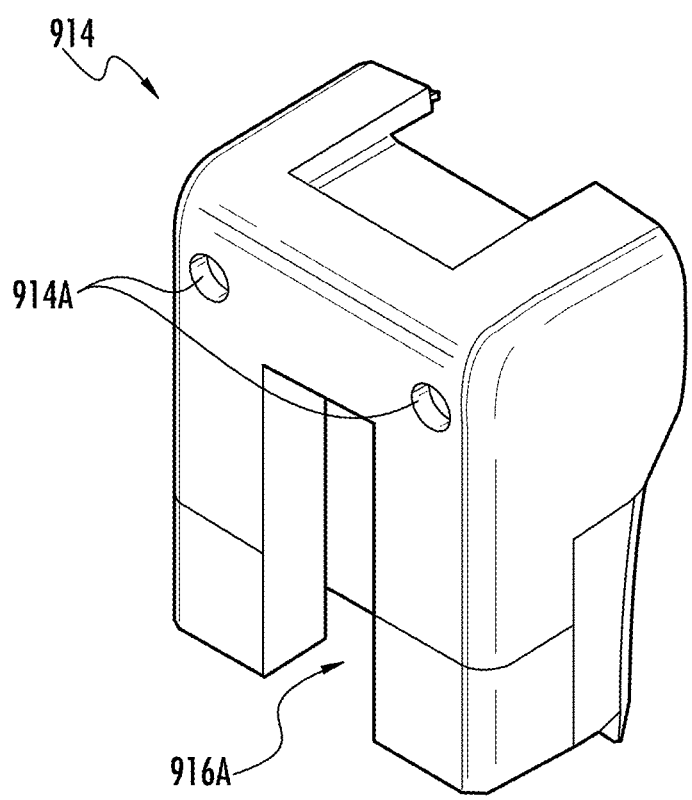
FIG. 20 shows an example of a base on the device.

FIG. 20 includes the details of the central base 914 between the base lid 926 and the distal vertical portion 917. The central base 914 connects to the base lid 926 on one side with all of the above referenced components enclosed between them.

Figure 21:
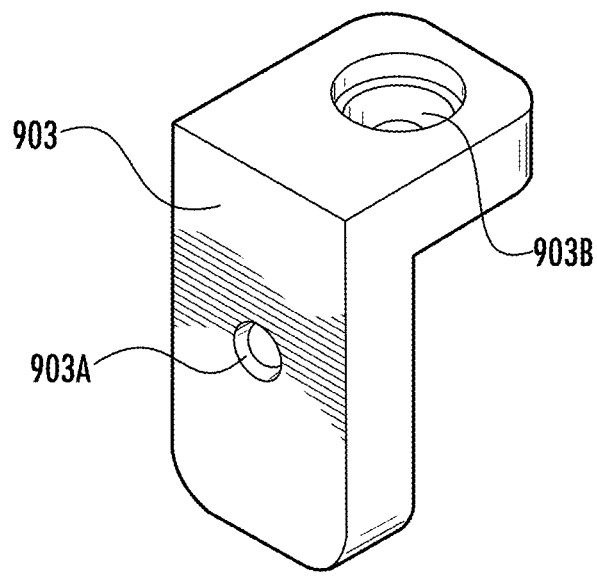
FIG. 21 shows an example of an adapter block for the device.

FIG. 21 shows one embodiment of the charger adapter block 903, which is found within the base lid 926 and serves as a mounting surface for the USB charger 902. The charger adapter block 903 may also be attached to a battery, which could be a Li-Ion battery 905, and a micro-processor 908.

Figure 22:
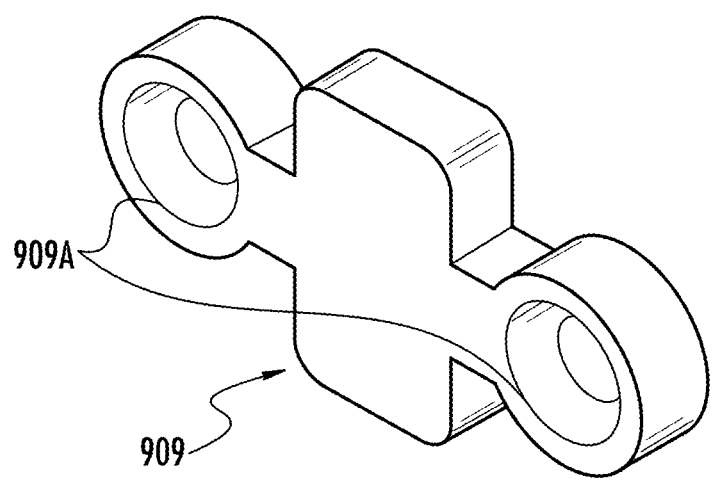
FIG. 22 shows an example of a potentiometer hold down on the device.

FIG. 22 shows one embodiment of the potentiometer hold down 909. The potentiometer hold down 909 secures the potentiometer base 910, which then secures a potentiometer arm 911 and adapter in place 912. The potentiometer hold down 909 may have fastener holes to be used with screws or similar fastening methods known in the art to be fastened to the above components.

Figure 23:
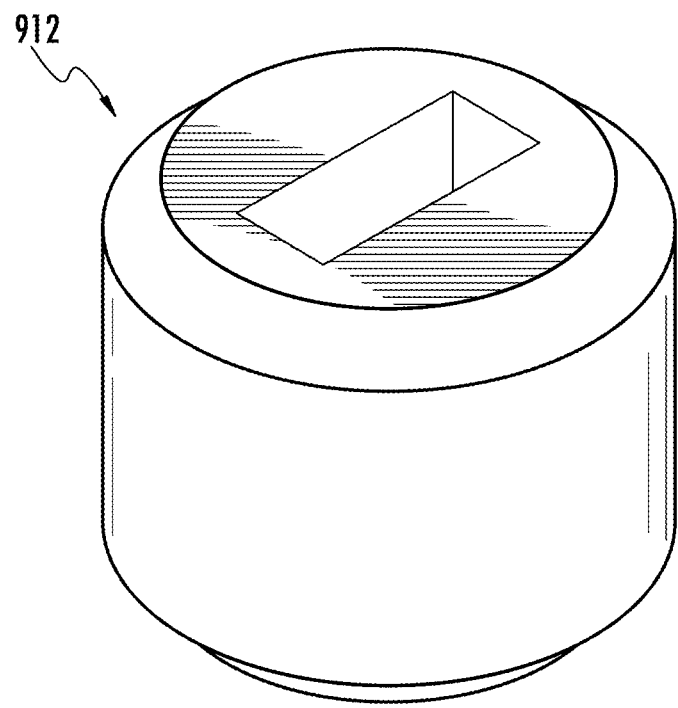
FIG. 23 shows an example of a potentiometer adapter on the device.

FIG. 23 shows one embodiment of the potentiometer adapter 912, which is situated between the potentiometer base 910 and the potentiometer arm 911, as shown in FIG. 17.

Figure 24:
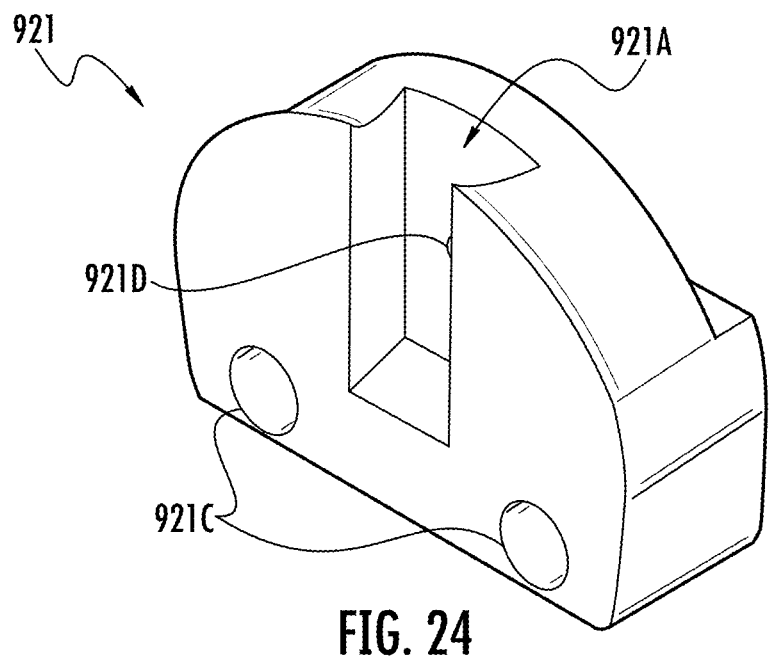
FIG. 24 shows an example of a track capture on the device.

FIG. 24 shows one embodiment of the track capture 921. The track capture 921 may be attached to the central base 914, and may be attached by socket head screws 923. The roller mount 916 may be positioned between the track capture 921 and the central base 914. A compression spring hole 921B may hold a compression spring in place between the track capture 921 and the roller mount 916. The track capture 921 may include a dovetail receptacle of the track capture 921A to accommodate the attachment of the various components for the joints on which the device will be used, as will be discussed herein and shown in FIGS. 27-31.

Figure 25:
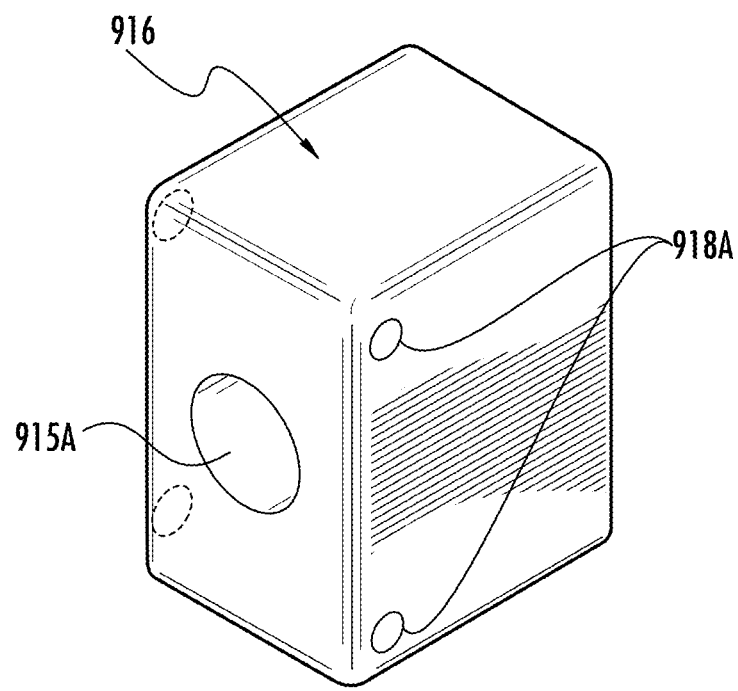
FIG. 25 shows an example of roller mount on the device.

FIG. 25 shows one embodiment of a roller mount 916. It is housed between the central base and the track capture. The roller mount 916 may have at least three holes 918A and 915A, these holes to be used to connect both the track rollers 918 and the knob 915 that passes through the distal vertical portion 917 to the roller mount 916. Two of the holes 918A are for the track rollers 918. One of the holes 915A is for the knob 915 that passes through the distal vertical portion 917.

Figure 26:
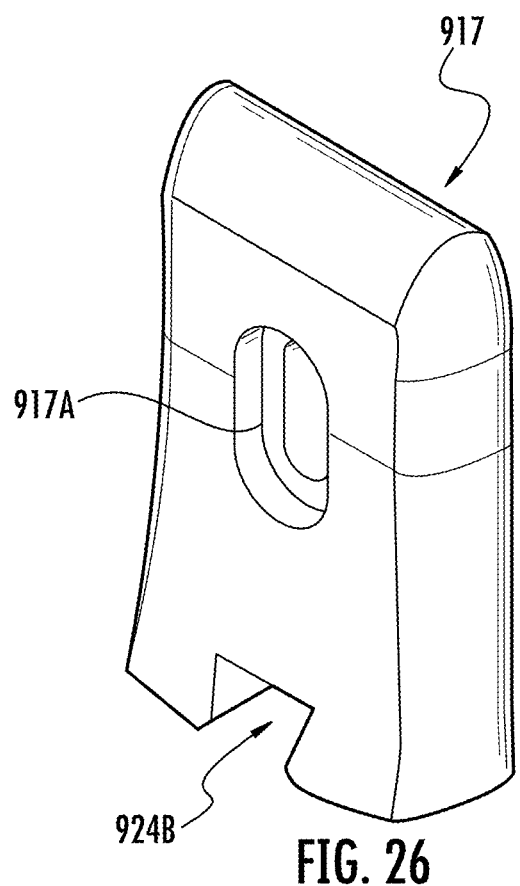
FIG. 26 shows an example of a distal base.

FIG. 26 shows one embodiment of the distal vertical portion 917. Positioned between the central base 914 and the distal vertical portion 917 is the roller mount 916, the track roller 918, and the track capture 921. The distal vertical portion 917 includes at least one hole 917A for the base adjusting knob 915 and a dovetail receptacle 924B for the attachment of various components that can be added to and used with the device to stabilize the joint in the use of the device, as discussed herein and shown in FIGS. 27-35.

The device battery 905, display 906 and microprocessor 908 of the device 900 include all of the features previously described for the battery 70, display 68 and microprocessor 66 of the glove 20, which descriptions are incorporated herein by reference.

Thus, as one method of use, pressure on the distal vertical portion 917 moves the distal vertical portion 917 down via the roller mechanism. In all of the herein described embodiments, this invention has the advantage that the user is in contact with the patient while performing the mobilization or linear translation. The user can see the patient's face and also feel the relevant soft tissue, thus, able to receive qualitative soft tissue feedback all while measuring the joint movement. The user never loses visual or touch contract with the patient during the mobilization.

Figure 27:
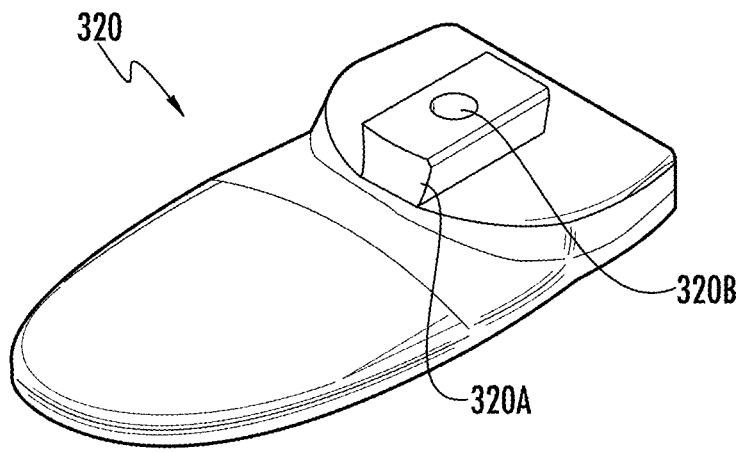
FIG. 27 shows an example of a contoured attachment for a wrist.

The microprocessor, which could be an Arduino board, sends a small current to the linear potentiometer and measures the resistance, which changes depending upon the vertical position of the rollers. The corresponding voltage drop recorded is indexed against a distance range prescribed, in this case, anywhere from 0.0 to 20 mm. Data processing and storage is accomplished via an Arduino board. The results could be outputted and displayed to an LCD screen on the external housing. The device could also include an auditory mechanism, to alert the user of the range of movement. In a further embodiment of the device 900, there are wireless capabilities, the data could be transmitted and stored by a computer application, which results could also be transmitted to the patient so that the clinician and/or patient could view any test results or progress and/or could see goals or treatments plans for the patient. The treatment sessions could also be connected to a billing application. The device could also include special attachments or embodiments that are configured to measure joint movement for specific body parts and types. For example, FIG. 27 shows one embodiment of a wrist component 320 that could be used with the device 900, which is designed to more conveniently and accurately measure joint movement in a wrist. The wrist component 320 is specially contoured such that it more readily and easily can be placed flush to the upper side or underside of a patient's wrist, and then used similar to the devices described herein with the same features and functionality. The wrist component 320 includes a dovetail flange 320A to snap into a dovetail receptacle 924B of the distal vertical portion 917. A spring plunger receptacle 320B helps secure the wrist component 320 once it is in place.

Figure 28:
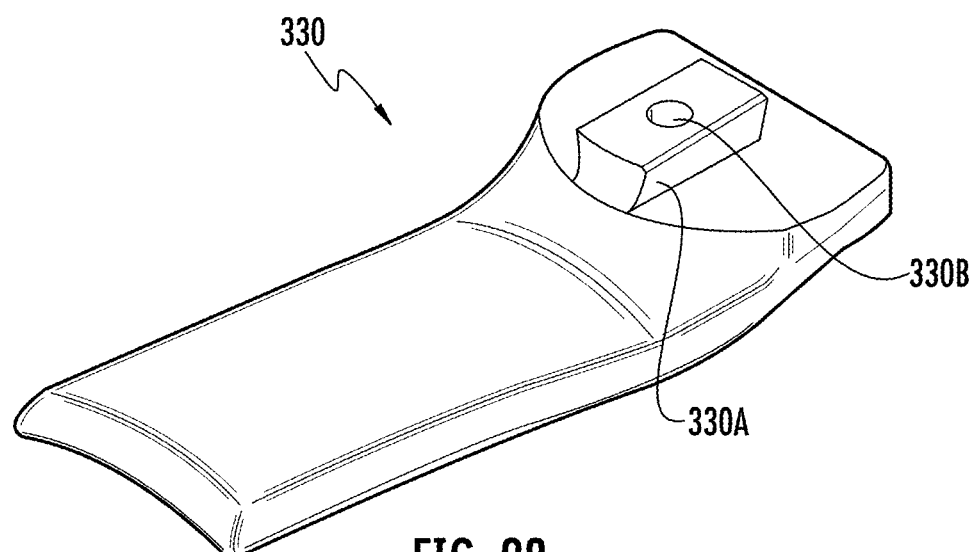
FIG. 28 shows an example of a contoured attachment for a knee.

FIG. 28 shows one embodiment of a knee component 330 that could be used with the device 900, which is designed to more conveniently and accurately measure joint movement in a knee. The knee component 330 is specially contoured such that it more readily and easily can be placed flush to a patient's knee, and then used similar to the devices described herein with the same features and functionality. It includes a dovetail flange 330A to snap into the dovetail receptacle 924B of the distal vertical portion 917. The spring plunger receptacle 330B helps secure the knee component 330 once it is in place.

Figure 29:
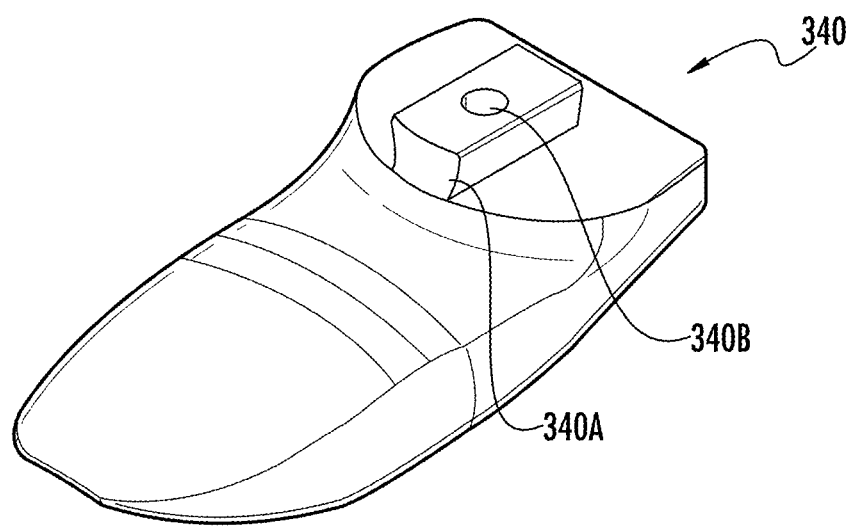
FIG. 29 shows an example of a contoured attachment for an ankle.

FIG. 29 shows one embodiment of an ankle component 340 that could be used with the device 900, which is designed to more conveniently and accurately measure joint movement in an ankle. The ankle component 340 is specially contoured such that it more readily and easily can be placed flush to a patient's ankle, and then used similar to the devices described herein with the same features and functionality. It includes a dovetail flange 340A to snap into the dovetail receptacle 924B of the distal vertical portion 917. The spring plunger receptacle 340B helps secure the ankle component 340 once it is in place.

Figure 30:
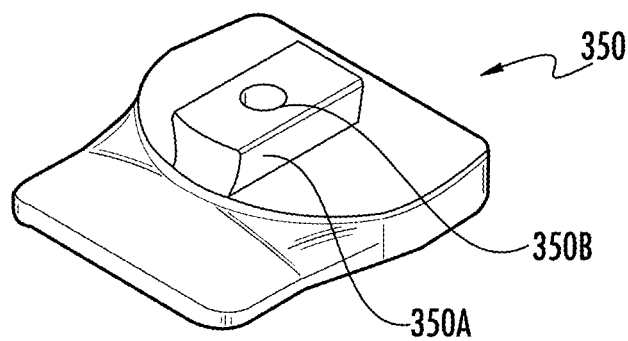
FIG. 30 shows an example of a contoured attachment for a shoulder.

FIG. 30 shows one embodiment of a shoulder component 350 that could be used with the device, which is designed to more conveniently and accurately measure joint movement in a shoulder. The shoulder component 350 is specially contoured such that it more readily and easily can be placed flush to a patient's shoulder, and then used similar to the devices described herein with the same features and functionality. It includes a dovetail flange 350A to snap into the dovetail receptacle 924B of the distal vertical portion 917. The spring plunger receptacle 350B helps secure the shoulder component 350 once it is in place.

Figure 31:
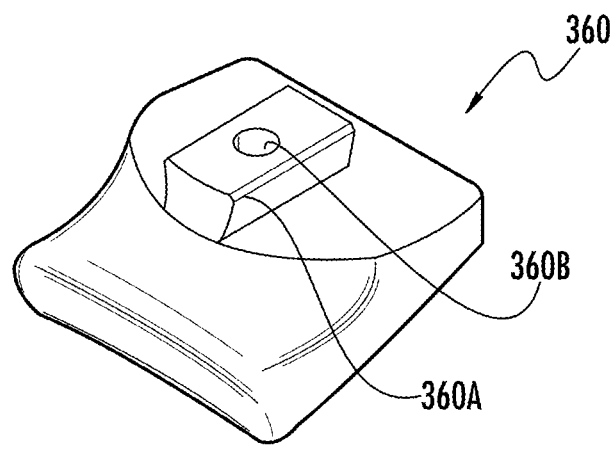
FIG. 31 shows an example of a contoured attachment for an elbow.

FIG. 31 shows one embodiment of an elbow component 360 that could be used with the device 900, which is designed to more conveniently and accurately measure joint movement in an elbow. The elbow component 360 is specially contoured such that it more readily and easily can be placed flush to a patient's elbow, and then used similar to the devices described herein with the same features and functionality. It includes a dovetail flange 360A to snap into the dovetail receptacle of the distal vertical portion 917. The spring plunger receptacle 360B helps secure the elbow component 360 once it is in place.

As one skilled in the art would appreciate, other components could also be used to more conveniently and accurately measure joint movement in other joints. Furthermore, these components could be sized to better fit adult or pediatric or animal patients.

Figure 32:
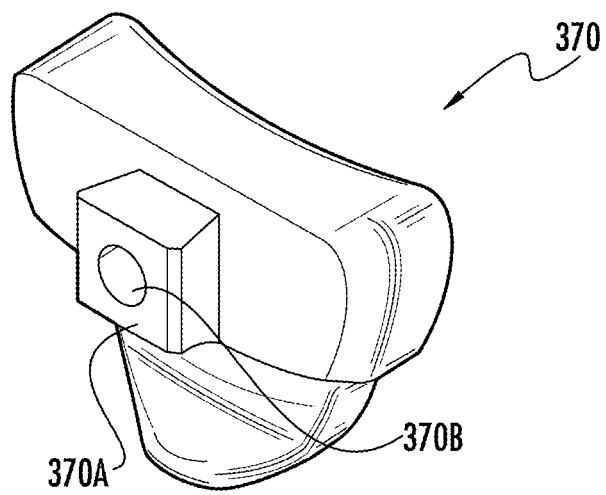
FIG. 32 shows an example of a small distal base attachment.
Figure 33:
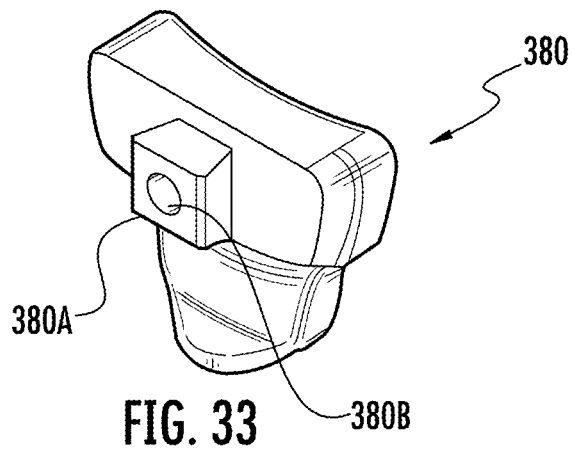
FIG. 33 shows an example of a large distal base attachment.

The device 900 may also have separate, specially sized distal base attachments for use with the device. FIGS. 32 and 33 show two separate embodiments of a contoured distal base attachment, one of smaller scale 370 (FIG. 32), and one of larger scale 380 (FIG. 33). In FIG. 32, the contoured distal base attachment 370 has a dovetail contour 370A used to accommodate the dovetail receptacle 924B on the distal vertical portion 917. This serves as the attachment of the various components used to stabilize the joint in the use of the device 900. Like the dovetail on the track capture 921D, there is a spring plunger hole 924A on the distal base and a spring plunger receptacle 370B to help secure this component to the device 900. In FIG. 33, the larger scale contoured distal base attachment 380 for use with the device 900 may have a similar dovetail contour 380A used to accommodate the dovetail receptacle 924B on the distal vertical portion 917. This dovetail receptacle 924B may serve as one means to attach various specialized components used to stabilize the joint in the use of the device 900. It also may include a spring plunger receptacle 380B to help secure the component on the device. In another embodiment, the specialized attachments may be adjustable or may be able to expand or contract to better fit the joint and patient.

Figure 34:
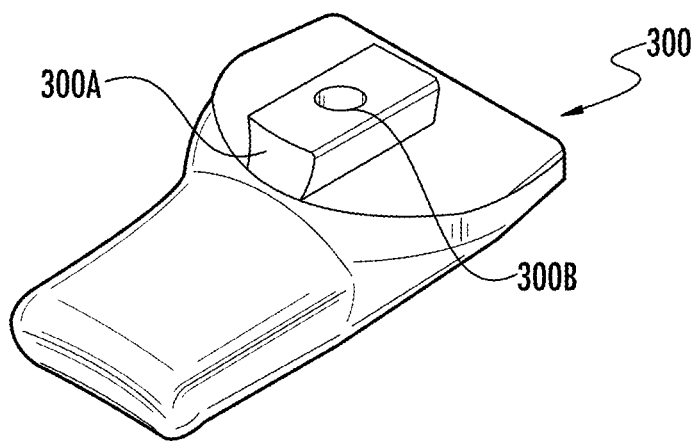
FIG. 34 shows an example of a large veterinary attachment.

The device 900 may also include specially sized and shaped or contoured attachments such that the device could be used to measure joint movement on animals. FIG. 34 shows one example of the larger of two contoured distal base attachments 300 for veterinary use on this device 900. It has a dovetail contour 300A used to accommodate the dovetail receptacle 924B on the distal vertical portion 917. This serves as the mechanism for attachment of the various components used to stabilize the joint in the use of the device.

Figure 35:
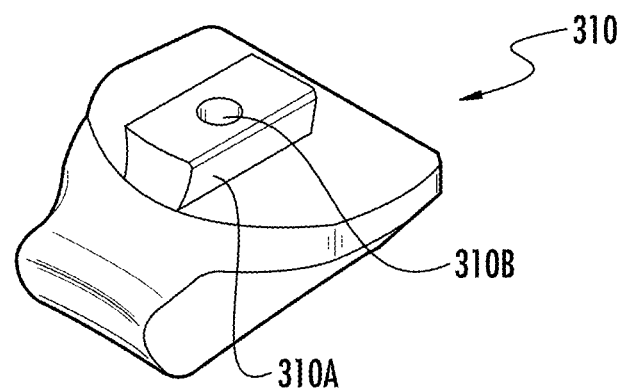
FIG. 35 shows an example of a small veterinary attachment.

FIG. 35 shows one example of a smaller version of a contoured distal base attachment 310 for veterinary use. It has a dove tail contour 310A used to accommodate the dovetail receptacle 924B on the distal base. This serves as the mechanism for attachment of the various components used to stabilize the joint in the use of the device. There is a spring plunger hole 310B on the distal vertical portion 917.

The described embodiments have the advantage of being lightweight, with the housing along with the components being portable and weighing less than 1 pound. The device is fully portable and can be used be a single practitioner.

FIGS. 36, 37A, 37B, 38, 38A, 38B, 39, 39C, and 39D show another embodiment of the invention that is a mechanical device 3600. Operators or companies may gamma radiate or otherwise subject the mechanical device 3600 to sterilization techniques that might harm sensitive electronics inside the device 900 above, and it may also meet the market need for an economical single use device.

Like the electronic device 900, the mechanical device 3600 measures linear translation of a joint, i.e. arthrokinematics gliding, with a preferred measurement being millimeters. This is different than angular measures (in degrees) of joint osteokinematics, i.e. flexion, extension, rotation. The measurement excursion may be 15 mm, which is sufficient for the assessment of all joints of the body.

FIGS. 36, 37A, and 37B show exploded and assembled views of the mechanical device 3600. Assembled as shown in FIGS. 37A and 37B, the device includes a main base body portion 3700 (comprising two halves 3701, 3707) joined together and housing multiple parts discussed hereafter including a support plate 3790 that supports the measurement spools and other parts as shown. The main base body 3700 is engaged to a proximal body portion 3800 via engagement of rollers 3820 within slot 3825. The main base body portion 3700 and proximal body portion 3800 include attachments 3610, 3810 respectively removeable from their body portions and may conform to other joints or sizes of joints. The attachments 3610, 3810 may include strap slots 3615, 3815 that allow for engagement of the attachments to a patient.

FIGS. 38, 38A, and 38B show the mechanical device 3600 in its zero-measurement position, ready to measure, and FIGS. 39, 39A, and 39B show it in its maximum 14 mm measurement position. Moving between these positions, the following occurs.

At first, a technician aligns the mechanical device 3600 on a patient, with its seam 3630 between the distal base 3700 and proximal portion 3800 aligned on a joint as discussed above. The technician then pulls the distal base portion 3700 relative to the proximal portion 3800 (while maintaining contact with the joint) as the proximal base portion rollers 3820 roll within a roller receiving slot 3825 within the distal base 3700 against a rolling surface 3703 thereof. A proximal gear rack 3830 is attached to and moves with the proximal portion 3800, and when the proximal portion 3800 moves, the proximal gear rack 3830 has teeth 3835 engaged pinion gear teeth 3735 on the pinion gear 3730. The pinion gear 3730's rotation also rotates the measurement tape spool 3740 through a a ring and sun gear engagement between the spool gear 3742 with teeth 3745 and pinion gear teeth 3734.

As the measurement spool 3740 rotates, it pulls the measurement tape 3750 and wraps the measurement tape 3750 around the measurement tape spool 3740. As the measurement tape 3740 moves, the measurement marking 3785 3755 advances beneath the measurement scale 3760 that is printed on a transparent medium (and base housing scale area 3705, which is also transparent), indicating the displacement measurement in 0.5 and 1.0 mm on the right scale 3764 and 0.25 and 1.0 mm on the left scale 3762.

The pin drive-max measurement assembly 3770 is keyed to the output shaft 3747 of the measurement tape spool 3740 and rotates therewith. As the pin drive output shaft 3747 rotates, it drives the measurement spool-max 3755 to rotate with it. The max measurement release pawl 3758 is biased such that its engagement portion 3758 engages the gear teeth 3757 3755 and slides over those teeth when rotating clockwise and otherwise locks the measurement max tape 3780 in place for reading on the right side 3764 of scale 3760 using indicator 3785.

When the distal side 3610 and base 3700 is released and allowed to come back to its zero position, the release pawl 3758 prevents the measurement spool-max 3755 from returning to its zero position, effectively holding the maximum measurement for the therapist. The release pawl 3758 can be actuated at any point by toggling the release button 3759 to allow the measurement spool-max 3755 to return to its zero position under its own bias.

The gearing within the main housing may be considered to be a mechanical measurement gearing and obviate the need for electronic sensors.

The mechanical device 3600 is capable of providing two measurements of displacement of a joint. A "live" measurement is constantly measured based on the position of the distal/base side of the device 3600 relative to the proximal base side 3800 and a "max" measurement that is the maximum displacement measured over multiple measurements until the maximum measurement release pawl 3770 is activated to zero the maximum measurement.

While the invention has been described with reference to the embodiments above, a person of ordinary skill in the art would understand that various changes or modifications may be made thereto without departing from the scope of the claims.

What is claimed is:

1. A device configured to measure joint mobilization during a mobilization procedure on a joint, comprising:
    a main base body portion;
    a proximal body portion engaged to the main base body portion through rollers and slots such that the main base body portion and proximal body portion are configured to move relative to the proximal body portion and main base body portion respectively;
    a mechanical measurement gearing configured to move a measurement spool when the main base body portion and proximal body portion move with respect to the proximal body portion and main base body portion respectively; and
    a measurement tape configured to move when the mechanical measurement gearing moves to indicate a measure of movement of the main base body portion and proximal body portion to the proximal body portion and main base body portion respectively.

2. The device of claim 1, wherein the main base body includes a measurement scale and the measurement tape includes a measurement indicator, wherein the measurement tape moves the measurement indicator during movement of the mechanical gearing and the measurement indicator moves relative to the measurement scale.

3. The device of claim 2, wherein the mechanical gearing includes a measurement spool engaged to a pinion gear and the proximal body portion includes a gear rack, wherein the pinion gear and gear rack are configured to engage the gear rack and pinion gear respectively through teeth thereon, wherein movement of the main base body portion and proximal body portion relative to the proximal body portion and main base body portion respectively is configured to move the gear rack and turn the pinion gear, which in turn are configured to turn the measurement spool.

4. The device of claim 3, wherein the measurement spool is configured to engage the measurement tape and configured to spool the measurement tape.

5. The device of claim 3, wherein the measurement spool and pinion gear are configured to engage the pinion gear and the measurement spool respectively in a ring and sun gear engagement.

6. The device of claim 4, further comprising a maximum measurement tape that moves when the mechanical measurement gearing moves and indicates a maximum measure of movement of the main base body portion and proximal body portion to one another, wherein the maximum measurement tape includes a maximum measurement indicator, wherein the maximum measurement tape moves the maximum measurement indicator during movement of the mechanical gearing and the maximum measurement indicator moves relative to the scale.

7. The device of claim 6, wherein the mechanical gearing includes a maximum measurement spool configured to engage the pinion gear, wherein the main base body portion and proximal body portion are configured to move relative to the proximal body portion and main base body portion respectively and move the gear rack and turn the pinion gear, which in turn are configured to turn the maximum measurement spool.

8. The device of claim 7, wherein the maximum measurement spool includes teeth thereon that are configured to engage a pawl, such that when movement of the main base body portion and the proximal body portion stops, the pawl is configured to engage the maximum measurement spool teeth and configured to hold the maximum measurement indicator in place until the pawl is released.

9. The device of claim 2, wherein the measurement scale is printed on a transparent medium.

10. The device of claim 1, wherein the rollers are included on the proximal base body and slots are roller receiving slots included in the main base body.

11. The device of claim 1, wherein the main base body portion is engaged to a main base attachment that is shaped to fit an anatomy of a person.

12. The device of claim 11, wherein the proximal body portion is engaged to a proximal body attachment that is shaped to fit an anatomy of a person.

13. The device of claim 12, wherein the main base attachment and proximal body attachment are removably attached to the main base body and proximal body respectively.

14. A method for measurement of linear translation of a joint comprising:
    providing a medical device of claim 1;
    aligning a seam between the main base body portion and the proximal body portion at the joint;
    securing the main base body portion and proximal body portion to a patient's body on either side of the joint;
    moving one side of the joint in arthrokinematics gliding movement such that the main base body portion and proximal body portion move relative to the proximal body portion and main base body portion respectively; and
    reading measure of movement from the measurement tape.

15. The method of claim 14, wherein the main base body portion is engaged to a main base attachment that is shaped to fit an anatomy of the patient's body.

16. The method of claim 15, wherein the proximal body portion is engaged to a proximal body attachment that is shaped to fit an anatomy of the patient's body.

17. The method of claim 16, wherein the main base attachment and proximal body attachment are removably attached to the main base body and proximal body respectively.

18. The method of claim 14, wherein the main base body includes a measurement scale and the measurement tape includes a measurement indicator, wherein the measurement tape moves the measurement indicator during movement of the mechanical gearing and the measurement indicator moves relative to the measurement scale.

19. The method of claim 18, wherein the mechanical gearing includes a measurement spool engaged to a pinion gear and the proximal body portion includes a gear rack, wherein the pinion gear and gear rack engage the gear rack and the pinion gear respectively through teeth thereon, wherein movement of the main base body portion and proximal body portion relative to the proximal body portion and the main base body portion moves the gear rack and turns the pinion gear, which in turn turns the measurement spool.

20. The method of claim 19, wherein the measurement spool is engaged to the measurement tape and spools the measurement tape.

* * * * *